(12) United States Patent
Archer

(10) Patent No.: US 8,346,485 B2
(45) Date of Patent: Jan. 1, 2013

(54) METHODS AND APPARATUSES FOR ESTIMATING INITIAL TARGET NUCLEIC ACID CONCENTRATION IN A SAMPLE BY MODELING BACKGROUND SIGNAL AND CYCLE-DEPENDENT AMPLIFICATION EFFICIENCY OF A POLYMERASE CHAIN REACTION

(75) Inventor: Benedict G. Archer, Vallejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 898 days.

(21) Appl. No.: 12/330,442

(22) Filed: Dec. 8, 2008

(65) Prior Publication Data

US 2010/0138198 A1    Jun. 3, 2010

Related U.S. Application Data

(60) Provisional application No. 61/117,926, filed on Nov. 25, 2008.

(51) Int. Cl.
*G06F 19/20* (2011.01)
(52) U.S. Cl. .................................................. 702/19
(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,965,188 A | 10/1990 | Mullis et al. |
| 5,219,727 A | 6/1993 | Wang et al. |
| 5,389,512 A | 2/1995 | Sninsky et al. |
| 5,476,774 A | 12/1995 | Wang et al. |
| 6,303,305 B1 | 10/2001 | Wittwer et al. |
| 6,503,720 B2 | 1/2003 | Wittwer et al. |
| 6,518,025 B1 | 2/2003 | Steinborn et al. |
| 6,551,783 B1 | 4/2003 | Carey |
| 6,691,041 B2 | 2/2004 | Sagner et al. |
| 6,713,297 B2 | 3/2004 | McMillan et al. |
| 6,783,934 B1 | 8/2004 | McMillan et al. |
| 6,830,887 B2 | 12/2004 | Lacroix |
| 6,902,900 B2 | 6/2005 | Davies et al. |
| 6,911,327 B2 | 6/2005 | McMillan et al. |
| 7,125,691 B2 | 10/2006 | Sagner et al. |
| 7,188,030 B2 | 3/2007 | Ward et al. |
| 7,228,237 B2 | 6/2007 | Woo et al. |
| 7,252,937 B2 | 8/2007 | Kaltenboeck |
| 7,267,942 B2 | 9/2007 | Peiris et al. |
| 7,276,358 B1 | 10/2007 | Zhu |
| 2002/0106653 A1 | 8/2002 | Kurane et al. |
| 2003/0087397 A1 | 5/2003 | Klein et al. |
| 2003/0104438 A1 | 6/2003 | Eyre et al. |
| 2003/0124512 A1 | 7/2003 | Stuyver |
| 2003/0129637 A1 | 7/2003 | Steinborn et al. |
| 2003/0148332 A1 | 8/2003 | Taylor et al. |
| 2003/0219788 A1 | 11/2003 | Kaltenboeck |
| 2003/0224351 A1 | 12/2003 | Overturf et al. |
| 2004/0096819 A1 | 5/2004 | McMillan et al. |
| 2005/0009009 A1 | 1/2005 | Peiris et al. |
| 2005/0069904 A1 | 3/2005 | Peirson et al. |
| 2005/0089862 A1 | 4/2005 | Therianos et al. |
| 2005/0158722 A1 | 7/2005 | Whelan et al. |
| 2005/0255516 A1 | 11/2005 | McMillan et al. |
| 2006/0047443 A1 | 3/2006 | Namkoong et al. |
| 2006/0088844 A1 | 4/2006 | Xu |
| 2006/0286587 A1 | 12/2006 | Lee et al. |
| 2007/0196824 A1 | 8/2007 | Stuyver et al. |
| 2007/0237716 A1 | 10/2007 | Mason et al. |
| 2009/0068666 A1 | 3/2009 | Bartkowiak et al. |
| 2009/0136951 A1 | 5/2009 | Hart et al. |

FOREIGN PATENT DOCUMENTS

| | | |
|---|---|---|
| DE | 100 45 521 | 10/2001 |
| EP | 0 959 140 | 11/1999 |
| EP | 1 013 775 | 6/2000 |
| EP | 1 138 784 | 10/2001 |
| EP | 1 288 314 | 3/2003 |
| EP | 1 295 941 | 3/2003 |
| EP | 1 619 258 | 1/2006 |
| EP | 1 185 695 | 7/2006 |
| EP | 1 395 681 | 7/2006 |
| EP | 1 722 309 | 11/2006 |
| EP | 1 495 136 | 12/2006 |
| EP | 1 788 097 | 5/2007 |
| EP | 1 849 877 | 10/2007 |
| FR | 2810049 | 12/2001 |
| GB | 2 402 212 | 12/2004 |
| JP | 2001-286300 | 10/2001 |
| JP | 2002-119291 | 4/2002 |
| JP | 2002-191372 | 7/2002 |
| JP | 2003-180378 | 7/2003 |
| JP | 2003-210199 | 7/2003 |

(Continued)

OTHER PUBLICATIONS

Gevertz, J. L., Dunn, S. M. & Roth, C. M. Mathematical model of real-time PCR kinetics. Biotechnol. Bioeng. 92, 346-355 (2005).*
Ranganathan, A. The Levenberg-Marquardt algorithm. Electronic document (2006). URL http://citeseerx.ist.psu.edu/viewdoc/summary?doi=10.1.1.10.2258.*
Yuan, J. S., Wang, D. & Stewart, C. N. Statistical methods for efficiency adjusted real-time PCR quantification. Biotechnology Journal 3, 112-123 (2008).*
Stolovitzky and Cecchi, Efficiency of DNA replication in the polymerase chain reaction. Proc. Natl. Acad. Sci. 1996, 93:12947-12952.
Rutledge et al., A kinetic-based sigmoidal model for the polymerase chain reaction and its application to high-capacity absolute quantitative real-time PCR. BMC Biotechnology, 8:47, 1-28, 2008.
Rebrikov and Trofimov, Real-time PCR: A review of approaches to data analysis. Applied Biochemistry and Microbiology, 42(5): 455-463, 2006.
International Search Report for PCT Patent Application No. PCT/US2009/065586 (Date of mailing Mar. 3, 2010).
Smith et al., Absolute estimation of initial concentrations of amplicon in a real-time RT-PCR process. BMC Bioinformatics, 8:409, p. 1-11, 2007.

*Primary Examiner* — Marjorie Moran
*Assistant Examiner* — Soren Harward
(74) *Attorney, Agent, or Firm* — Foley & Lardner LLP

(57) ABSTRACT

Provided are methods for estimating the amount of initial target nucleic acid in a sample prior to nucleic acid amplification by polymerase chain reaction (PCR). The methods generally involve modeling signal intensity data generated across a range of PCR cycles with a phenomenological model in concert with a chemical model, to yield an estimate of the amount of initial target nucleic acid in the sample.

23 Claims, 8 Drawing Sheets

FOREIGN PATENT DOCUMENTS

| | | |
|---|---|---|
| JP | 2003-334078 | 11/2003 |
| JP | 2004-248678 | 9/2004 |
| JP | 2004-267215 | 9/2004 |
| JP | 2004-305219 | 11/2004 |
| JP | 2006-075167 | 3/2006 |
| JP | 2004-000203 | 1/2008 |
| WO | WO-97/46707 | 12/1997 |
| WO | WO-99/40219 | 8/1999 |
| WO | WO-99/54510 | 10/1999 |
| WO | WO-00/41549 | 7/2000 |
| WO | WO-00/44935 | 8/2000 |
| WO | WO-01/31056 | 5/2001 |
| WO | WO-01/32909 | 5/2001 |
| WO | WO-01/44280 | 6/2001 |
| WO | WO-02/08414 | 1/2002 |
| WO | WO-03/012142 | 2/2003 |
| WO | WO-03/029924 | 4/2003 |
| WO | WO-03/048377 | 6/2003 |
| WO | WO-03/068918 | 8/2003 |
| WO | WO-03/070980 | 8/2003 |
| WO | WO-03/089669 | 10/2003 |
| WO | WO-2004/085455 | 10/2004 |
| WO | WO-2005/062040 | 7/2005 |
| WO | WO-2005/067646 | 7/2005 |
| WO | WO-2005/081776 | 9/2005 |
| WO | WO-2005/106026 | 11/2005 |
| WO | WO-2006/037207 | 4/2006 |
| WO | WO-2006/135437 | 12/2006 |

* cited by examiner

METHODS AND APPARATUSES FOR ESTIMATING INITIAL TARGET NUCLEIC ACID CONCENTRATION IN A SAMPLE BY MODELING BACKGROUND SIGNAL AND CYCLE-DEPENDENT AMPLIFICATION EFFICIENCY OF A POLYMERASE CHAIN REACTION

CROSS-REFERENCE TO RELATED PATENT APPLICATIONS

This application claims priority to U.S. Application Ser. No. 61/117,926 filed Nov. 25, 2008, which is incorporated by reference herein in its entirety including all figures and tables.

FIELD OF THE INVENTION

The invention relates to methods for estimating the amount of a target nucleic acid (NA) in a sample prior to amplification by polymerase chain reaction.

BACKGROUND OF THE INVENTION

The following description of the background of the invention is provided simply as an aid in understanding the invention and is not admitted to describe or constitute prior art to the invention.

Polymerase chain reaction (PCR), is an in vitro enzymatic reaction for the amplification of a target nucleic acid (NA). PCR is commonly carried out as a thermally cyclical reaction; that is, a reaction tube is heated and cooled to achieve the temperatures required at each step of a replication reaction in a single PCR cycle. After each replication cycle, the generated NA itself becomes a template for replication in subsequent cycles. Thus, target NA in a sample grows exponentially over the course of repeated cycles. With PCR it is possible to amplify from as little as one or a few copies of a target NA to amounts several orders of magnitude greater.

Quantitative PCR (QPCR), also known as real-time PCR, typically utilizes fluoresce-based detection methods to monitor the quantity of a target NA after each amplification cycle. Various methods have been reported for analyzing signal indicative of the amount of amplicon at each cycle generated from such experiments. Perhaps most common are variations of the threshold (Ct) standard curve method. In this method, the generated signal is analyzed to determine a fractional cycle number that is related to initial template concentration. One example of such a method is described in U.S. Pat. No. 6,303,305 (Wittner et. al.).

Mathematical descriptions of the chemical reactions of a PCR cycle have also been reported. For example, Stolovitzky and Cecchi, *Proc. Natl. Acad. Sci.* 1996, 93:12947-52 described one mathematical model of the amplification efficiency of DNA replication in PCR developed from considering the kinetics of the chemical reactions involved.

SUMMARY OF THE INVENTION

The present invention provides methods for estimating the amount of a target nucleic acid (NA) in a sample prior to amplification by PCR by analysis of the results of the PCR process.

In one aspect, methods are provided for estimating the amount of initial target nucleic acid in a sample prior to nucleic acid amplification by polymerase chain reaction (PCR). Methods of this aspect include modeling signal intensity data generated across a range of PCR cycles with a phenomenological model in concert with a chemical model, to yield an estimate of the amount of initial target nucleic acid in the sample; and outputting an estimate of the amount of initial target nucleic acid in the sample to a user or computer readable format. In the phenomenological model, signal intensity is a function of background, initial target nucleic acid, and amplification efficiency defined as the fractional amount of target nucleic acid in a reaction mixture generated in a given PCR cycle; and in the chemical model, the fractional amount of target nucleic acid in a reaction mixture generated in a given PCR cycle is estimated from kinetic or equilibrium modeling of chemical reactions occurring in the given PCR cycle. In some embodiments of this aspect, the phenomenological model is in accordance with formula (1):

$$z_k = a + bk + Gx_o \prod_{i=1}^{k} (1 + E_i) \quad (1)$$

where the parameters $k$, $z_k$, $a$, $b$, $G$, $x_0$, and $E_i$ are defined as used in equations (6a) or (6b) and (1b) (in Description Section).

In some related embodiments, the background correction factors a and b are calculated by pre-analysis estimation with a model in accordance with formula (2):

$$z_k = a + bk + c(1+E_c)^k \quad (2)$$

where the parameters $k$, $z_k$, $a$, $b$, $c$, and $E_c$ are defined as used in equation (67).

In some embodiments, the chemical model is in accordance with formula (3):

$$P_3 = s^2 E^3 - (s^2 + (1-D+2q)s)E^2 + q(2s+q+1)E - q^2 = 0 \quad (3)$$

where E, s, q, and D are defined as used in equation (50) and (1b).

In some related embodiments, the background contribution to the signal intensity may be estimated concurrently with the estimation of parameters of formula (3). In some embodiments, the estimated initial target nucleic acid may be directly derived from the modeling of formula (1). Alternatively, the amount of initial target nucleic acid is estimated from the initial reduced single stranded nucleic acid concentration, $s_0$, according to formula (4):

$$s_o = x_o \frac{K_2}{NV} \quad (4)$$

where $s_0$, $x_0$, $K_2$, N, and V are defined as used in equation (70).

Alternatively, in some embodiments, the chemical model is in accordance with formula (5):

$$P_4 = s^3 E^4 - (s^3 + (p + 2\kappa q + 2\kappa)s^2)E^3 + \quad (5)$$
$$((p + 2\kappa q + \kappa)s^2 + ((2\kappa q + \kappa)p + \kappa + (-\kappa q - \kappa)^2)s)E^2 -$$
$$((2\kappa qp + (\kappa q + \kappa)\kappa q)s + (\kappa q + \kappa)\kappa qp + \kappa^2 q)E + \kappa^2 q^2 p = 0$$

where E, p, s, q, and K are defined as used in equations (9c) and (15a-d).

In some related embodiments, the background contribution to the signal intensity may be estimated concurrently with the estimation of parameters of formula (5). In some embodiments, the estimated initial target nucleic acid may be directly derived from the modeling of formula (1). Alternatively, the amount of initial target nucleic acid is estimated from the initial reduced single stranded nucleic acid concentration, $s_0$, according to formula (6):

$$s_o = x_o \frac{K_1}{NV} \qquad (6)$$

where $s_0$, $x_0$, $K_1$, N, and V are defined as used in equation (69).

Alternatively, in some embodiments, the chemical model is a chemical model expressible as formula (7):

$$P_2 = sE^2 - (s+q+1)E + q = 0 \qquad (7)$$

where E, s, q, and K are defined as used in equation (17) and (1b).

In some related embodiments, the contribution to the signal intensity from the background may be estimated concurrently with the estimation of parameters of formula (7). In some embodiments, the estimated initial target nucleic acid may be directly derived from the modeling of formula (1). Alternatively, the amount of initial target nucleic acid is estimated from the initial reduced single stranded nucleic acid concentration, $s_0$, according to formula (4):

$$s_o = x_o \frac{K_2}{NV} \qquad (4)$$

where $s_0$, $x_0$, $K_2$, N, and V are defined as used in equation (70).

In some embodiments of this aspect, modeling signal intensity data comprises a nonlinear least squares curve fitting approximation method for estimating parameters of the model formulas. In related embodiments, the nonlinear least squares approximation method may be a Levenberg-Marquardt approximation method.

In some embodiments of this aspect, the methods further comprise identifying a subset of signal intensity data generated across a range of PCR cycles for modeling. In related embodiments, identifying a subset may comprise identifying a range of PCR cycles beginning before replication is apparent and ending at a cycle where the amplification efficiency, $E_k$, has decreased to a predetermined absolute lower limit or a relative amount from the initial amplification efficiency, $E_1$; preferably the amplification efficiency of the ending cycle is between 10% and 50% of the initial efficiency. In related embodiments, the subset comprises the ending cycle and five to fifteen preceding cycles.

In other embodiments, the phenomenological model is expressed as formula (1); and the chemical model is expressed as a formula selected from the group consisting of formulas (3), (5), and (7). In some embodiments, the chemical model is expressed as formula (3); and background correction factors a and b are estimated in accordance with formula (67), prior to estimation of parameters of formula (3) and (7). In other embodiments, the chemical model is expressed as a formula selected from the group consisting of formula (5) and formula (7); and the background correction factors a and b are estimated concurrently with the estimation of parameters of the formula of the chemical model.

In a second aspect, a computer program product for estimating the amount of initial target nucleic acid in a sample is provided. In embodiments of this aspect, the computer program product is embodied on a computer-readable medium, the computer program product comprising computer code for receiving input indicative of an amount of target nucleic acid present in a sample at multiple times during a PCR amplification; and computer code for estimating the amount of initial target nucleic acid in the sample; wherein, the computer code for estimating the amount of initial target nucleic acid operates in accordance with formula (2) and a formula selected from the group consisting of formulas (3), (5), and (7). In some embodiments, the input is received from a user. In other embodiments, the input is received from a device.

In a third aspect, an apparatus for estimating the amount of initial target nucleic acid in a sample is provided. In embodiments of this aspect, the apparatus comprises a processor; and a memory unit coupled to the processor. In these embodiments, the memory unit includes computer code for receiving input indicative of an amount of target nucleic acid present in a sample at multiple times during a PCR amplification; and computer code for estimating the amount of initial target nucleic acid in the sample; wherein, the computer code for estimating the amount of initial target nucleic acid operates in accordance with formula (2) and a formula selected from the group consisting of formulas (3), (5), and (7). In some embodiments, the input is received from a user. In other embodiments, the input is received from a device.

The term "amount of initial target nucleic acid," or "amount of initial target NA," as used herein means the amount of target NA present in a sample prior to amplification by PCR. The amount of initial target NA may also be referred to as initial amount of target NA, or as the starting amount of the template in the sample that is subject to amplification in the PCR reaction. Amount of initial target NA is generally expressed in terms of a number of copies, moles, or mass. If the sample volume containing the amount of initial target NA is known, amount of initial target NA values may be expressed in various terms of concentration, such as copies of NA per volume, moles of NA per volume, or mass of NA per volume.

The term "polymerase chain reaction" as used herein means the well known polymerase chain reaction process as particularly described in U.S. Pat. Nos. 4,683,202; 4,683,195; and 4,965,188.

The term "model" as used herein refers to a mathematical or logical representation of a system of entities, phenomena, or processes. Implementation of a model may include deriving values of mathematical parameters contained within the model. Values of model parameters may be derived by any appropriate mathematical method known in the art.

The testis "phenomenological model" as used herein in reference to a PCR process refers to a mathematical representation of target NA amplification with no recognition of the underlying chemical reactions occurring in each PCR cycle. Parameters in a phenomenological model of a PCR process relate generally to the overall PCR process, such as, for example, amplification efficiency and background contribution to signal intensity.

The term "chemical model" as used herein refers to a mathematical representation of kinetic or equilibrium modeling of a system of chemical reactions. Chemical models may include parameters representing various attributes of the system, such as concentrations of reactants and products, and equilibrium and rate constants. In embodiments of the present invention, various chemical models are used to estimate amplification efficiency for PCR cycles. Chemical models of the present invention may include parameters such as total reduced concentrations of polymerase, primer, target NA, as well as equilibrium constants for the reactions that occur in a PCR cycle.

The term "amplification efficiency" or "efficiency," E, as used herein refers to the fractional amount of target NA present in an amplification reaction mixture after one or more PCR cycles that was generated in the reaction mixture by amplification. Amplification efficiency of a single PCR cycle, also referred to as the cycle dependent efficiency, is the fractional amount of target NA present in a reaction complex after a given PCR cycle that was generated in the reaction mixture by amplification at the given PCR cycle.

The term "about" as used herein in reference to quantitative measurements refers to the indicated value plus or minus 10%.

The summary of the invention described above is non-limiting and other features and advantages of the invention will be apparent from the following detailed description of the invention, and from the claims.

DETAILED DESCRIPTION OF THE INVENTION

Figure 1:
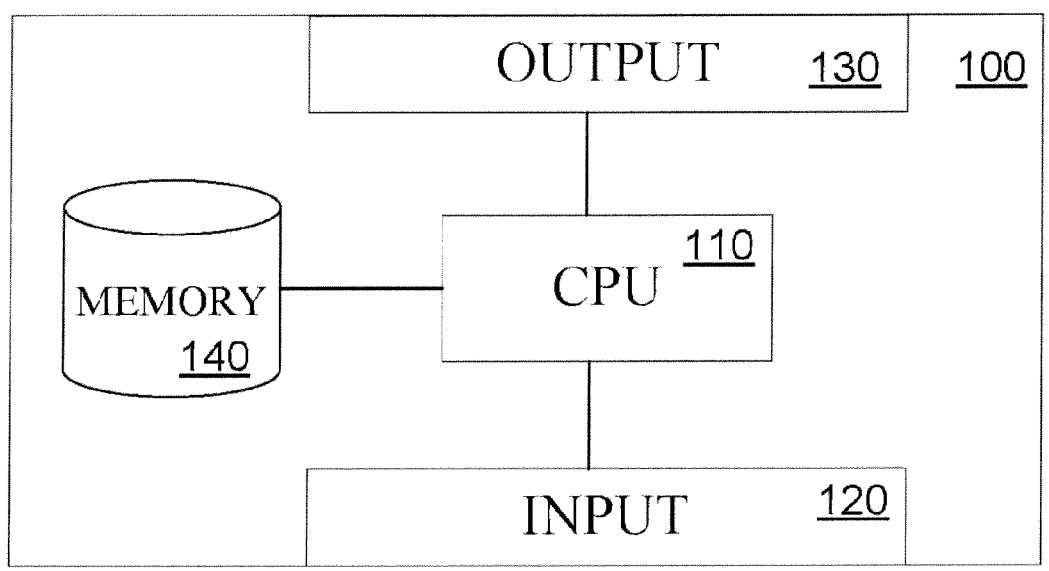
FIG. 1 is a schematic illustration of an exemplary device for implementation of a system that estimates target NA in a sample prior to NA amplification by QPCR.

Models of a PCR process useful for estimating initial target NA from data representative of the amount of amplicon generated in QPCR may fall into either of two general categories: phenomenological models or chemical models. Phenomenological models include parameters relating to the overall PCR process (i.e., target NA amplification) and generally model the process as a growth process with no recognition of the underlying physical or chemical mechanisms operating in each cycle. Chemical models, on the other hand, are based on the underlying chemistry, incorporating kinetic considerations, equilibrium considerations, or both, and include parameters representing attributes of the chemical mechanisms that are operating in each cycle.

Disclosed herein are methods with algorithms for estimating the initial amount of target NA in a sample from data representative of the amount of amplicon generated in QPCR. These methods may additionally be used to qualitatively assess the presence of target NA, which itself may be indicative of a disease state or condition. In preferred embodiments, the methods and algorithms of the present invention utilize a basic phenomenological model of the effect of amplification efficiency (E) and system background on raw, measured data (preferably fluorescence data); in concert with a chemical model of the equilibrium bindings of a primer to a single strand target NA to form a heteroduplex, and of a polymerase to the heteroduplex to form a replication complex (i.e., chemical models).

Both of the above equilibrium bindings considered in chemical models used in embodiments of the present invention can approach 100% at the start of a PCR cycling process when primer and polymerase concentrations are high and the number of target NA molecules is relatively low. However, with each successive cycle, the number of target NA molecules increases, primer concentration decreases, and polymerase activity possibly declines. All three of these changes potentially reduce E (i.e., the fractional amount of target NA that is incorporated into a reaction complex in a given step). Thus, chemical models employed in embodiments of the present invention estimate E for a PCR cycle based on chemical mechanistic models. Estimates of E for a PCR cycle may then be used in a phenomenological model to estimate the concentration of initial target NA in the sample.

While in some embodiments E is estimated for consecutive PCR cycles, it is understood that in other embodiments E may be estimated for fewer than all PCR cycles. For example, E may be estimated for two of every three cycles, every other cycle, or at any other sampling. Preferably, E is estimated for at least every second cycle within the subset of cycles analyzed.

In preferred embodiments, the phenomenological model is a combined PCR/background model. In some embodiments, the chemical model is a four parameter chemical model (chemical model A). In other embodiments, the chemical model is a two parameter chemical model (chemical model B). In yet other embodiments, the chemical model is a polymerase binding amplicon-primer competition chemical model (chemical model C). Development of these models follows.

Basic PCR Model

Each cycle in the PCR process includes: (a) melting double-stranded NA; (b) primer and polymerase binding to form a replication complex; and (c) templated primer extension. With perfect efficiency (E=1), each cycle would double the amount of NA, but realistic models include E as a parameter to be determined. This is because, as described above, several cumulative factors may inhibit amplification efficiency as the number of completed cycles increases. Denoting the amount of initial target NA in a sample as $x_0$ and target NA in the sample at the end of cycle k as $x_k$, the cyclical process is fairly represented as a recursion relating the target NA at the end of cycle k and the cycle dependent efficiency, $E_{k+1}$, to target NA at the end of cycle k+1 (the following cycle):

$$x_{k+1}=x_k+E_{k+1}x_k=x_k(1+E_{k+1}). \tag{1a}$$

Rearranging this relationship allows for expression of the cycle dependent efficiency, $E_{k+1}$, in terms of the fractional amount of target nucleic acid present in a reaction mixture at the beginning and end of an amplification cycle:

$$E_{k+1} = \left(\frac{x_{k+1}}{x_k}\right) - 1 \tag{1b}$$

Thus, the target NA after n cycles ($x_n$) is proportional to amount of initial target NA ($x_o$) according to the following relationship:

$$x_n = x_o \prod_{i=1}^{n} (1+E_i) \tag{2a}$$

This relationship can also be expressed in terms of the fractional amount of target nucleic acid present in a reaction complex at the beginning and end of one or more amplification cycles according to the following relationship:

$$x_n = x_o \prod_{i=1}^{n} \left(\frac{x_i}{x_{i-1}}\right) \tag{2b}$$

PCR Model Dependence on Reporter Type

Introduction of a system calibration factor, $R_{sys}$, into equation (2) provides conversion of the target NA after n cycles to net signal after n cycles ($y_n$):

$$y_k = R_{sys} x_o \prod_{i=1}^{k} (1+E_i) \tag{3a}$$

In a general sense, $R_{sys}$ accounts for the system characteristics necessary to relate detected signal to the amount of amplicon present at the time of detection. In a fluorescence-based quantitation system, $R_{sys}$ accounts for spectral attributes of reporter fluorophores and instrument optical and detection subsystem response characteristics. In such systems, $R_{sys}$ can be considered a unit conversion factor from target NA amount to fluorescence detection system units.

The relationships described in equations (2) and (3a) are applicable for real-time processes monitored by reporters that directly signal amounts of double-stranded NA such as intercalating or groove-binding dyes. However, for probes bearing an emitter-quencher pair which generates fluorescence signal only in the annealed state or when cleaved by polymerase 5' exonuclease activity, the signal at cycle k is proportional to the amount of target NA at the beginning of the cycle, i.e., the amount of target NA at the end of the previous cycle. In such a system, the relationship in equation (3a) becomes:

$$y_k = R_{sys} E_1 x_o \prod_{i=2}^{k} (1+E_i) \tag{3b}$$

or, in another form, $$y_k = R_{sys} \frac{E_1}{(1+E_1)} x_o \prod_{i=1}^{k} (1+E_i). \tag{3c}$$

Background Model

Raw, measured signal from a PCR process may include contributions from background processes. Signal arising from background processes would be a systematic bias if not separated from PCR signal before analysis by any model-based algorithm. However, as estimating and subtracting background from raw data is itself subject to error, in some embodiments of the present invention, a background model may be combined with a PCR model.

A background model that may be used in some embodiments of the present invention includes contributions from two terms, a and bk, representing background offset and constant drift after k cycles, respectively. Thus, one background model ($w_k$) that may be used in some embodiments of the present invention follows the equation:

$$w_k = a + bk \tag{4}$$

Combined PCR and Background Models

Combining the contributions to the raw, measured signal from the net signal (equation (3a) or (3c), depending on reporter type), and the background (equation (4)), leads to the following combined models:

$$z_k = a + bk + R_{sys} x_o \prod_{i=1}^{k} (1+E_i) \tag{5a}$$

or $$z_k = a + bk + R_{sys} \frac{E_1}{(1+E_1)} x_o \prod_{i=1}^{k} (1+E_i). \tag{5b}$$

For the sake of simplicity, these two equations may be generalized by introducing a system composite factor, G, which represents $R_{sys}$ or $$R_{sys} \frac{E_1}{(1+E_1)}$$

depending on reporter type used to generate the data to be analyzed. The generalized model is as follows:

$$z_k = a + bk + G x_o \prod_{i=1}^{k} (1+E_i). \tag{6a}$$

The same generalized model can be expressed without explicit use of the concept of efficiency (variable E) as follows:

$$z_k = a + bk + G x_o \prod_{i=1}^{k} \frac{x_i}{x_{i-1}}, \tag{6b}$$

which follows from equations (1b) and (6a).

Rewriting the generalized model in this way makes it clear that use of a particular variable or parameter for efficiency, while convenient, is not essential to any of the presently presented models. Furthermore, as $$\frac{x_i}{x_{i-1}}$$

is a unitless ratio of two quantity measures of identical units, ratios of any such measures such as moles, molarities, or other concentration scales could be used in evaluating $$\frac{x_i}{x_{i-1}}.$$

Chemical Models

In developing chemical models for efficiency estimation, the inventors started with the approach of Stolovitzky and Cecchi, *Proc. Natl. Acad. Sci.* 1996, 93:12947-52 and adopted some of their notation in modeling selected steps in the PCR cycle chemistry, but made simplifying assumptions to avoid an unmanageable number of parameters. Embodiments of the present invention include only equilibrium parameters, as one assumption is that cycle times are sufficient that, for the subset of cycles analyzed, reactions proceed to virtual equilibrium. A second assumption made for some, but not all, embodiments of the present invention is that template concentrations are low enough that the only annealing process occurring is primer binding and that polymerase activity is constant for all cycles. A third assumption is that triphosphosate nucleosides are in high enough concentration that formation of a template-primer-polymerase complex results in complete primer extension 100% of the time.

In the following description of chemical models used in embodiments of the present invention, single stranded nucleic acid is denoted as s, primer as p, primer-template duplex as $h_0$ (with the subscript indicating the number of nucleotides extending the primer), triphosphate nucleosides as n, polymerase by q, and reaction complex by r. The primer comprises L nucleotides, and template length is L+N. Thus, reactions in a PCR cycle (and their corresponding equilibrium expressions) included in chemical models used in certain embodiments of the present invention can be expressed as follows:

$$s + p \rightleftharpoons h_o \qquad K_1 = \frac{[h_o]}{[s][p]} \tag{7a}$$

$$q + h_o \rightleftharpoons r_o \qquad K_2 = \frac{[r_o]}{[q][h_o]} \tag{7b}$$

$$r_o + N_n \rightleftharpoons h_N + q \quad K_3 \approx \infty, [r_o] \approx 0. \tag{7c}$$

These lead to the expression of conservation relations amongst the products and reactants as follows:

$$[s]_T = [s] + [h] + [r] \tag{8a}$$

$$[p]_T = [p] + [h] + [r] \tag{8b}$$

$$[q]_T = [q] + [r]. \tag{8c}$$

In the above conservation relations, a subscripted $[\bullet]_T$ denotes a total concentration; absence of the subscript $_T$ denotes an equilibrium concentration. Integer subscripts on h and r are dropped as the last reaction above is assumed to go to completion. That is, [r] denotes a concentration of duplex molecules with fully extended primers.

Correspondences to PCR cycles, with subscript $[\bullet]_k$ indicating concentrations in cycle k, are:

Template at the start of cycle k: $[s]_{T,k}$ (9a)

Template at the end of cycle k: $[s]_{T,k}+[r]_k$ (9b)

Replication efficiency in cycle k: $E_k=[r]_k/[s]_{T,k}$ (9c)

Implementation of some embodiments of the present invention exploits the following recursions:

$$[s]_{T,k+1}=[s]_{T,k}+[r]_k \tag{10a}$$

$$[p]_{T,k+1}=[p]_{T,k}-[r]_k. \tag{10b}$$

Chemical Model A: Four Parameter Chemical Model

Equilibria (7a-c) were then solved for [h] and [r]:

$$[h] = \frac{[r]}{K_2[q]} \tag{11a}$$

$$[r] = K_1 K_2 [q][p][s]. \tag{11b}$$

This rearrangement allows for removal of [h] from the conservation relations in equations (8a-b):

$$[s]_T = [s] + \frac{[r]}{K_2[q]} + [r] \tag{12a}$$

$$[p]_T = [p] + \frac{[r]}{K_2[q]} + [r]. \tag{12b}$$

Equation (8c) was then be used to eliminate free polymerase concentration ([q]) from equations (10a-b), (11b), thereby reducing the model to a set of three equations:

$$[r] = K_1 K_2 ([q]_T - [r])[p][s] \tag{13a}$$

$$[s] = [s]_T - [r]\left(1 + \frac{1}{K_2([q]_T - [r])}\right) \tag{13b}$$

$$[p] = [p]_T - [r]\left(1 + \frac{1}{K_2[q]_T - [r]}\right). \tag{13c}$$

These three equations were then further reduced to a single equation with the substitution of E for the ratio $[r]_k/[s]_{T,k}$ (as defined in equation (9c)):

$$K_2([q]_T-E[s]_T)E[s]_T=K_1\{K_2([q]_T-E[s]_T)([s]_T-E[s]_T)-E[s]_T\}\times\{[p]_T K_2([q]_T-E[s]_T)([q]_T-E[s]_T)-E[s]_T\} \tag{14}$$

Equation (14) was then further transformed by transforming molar concentrations to reduced concentrations, s, p, and q, and including of a ratio of association constants, κ, according to the following equations:

$$s=K_1[s]_T \tag{15a}$$

$$p=K_1[p]_T \tag{15b}$$

$$q=K_2[q]_T \tag{15c}$$

$$\kappa=K_1/K_2 \tag{15d}$$

This allows equation (14) to be expressed as a fourth degree polynomial in E, whose coefficients are functions of four parameters (subscripts denoting cycle omitted for simplicity):

$$P_4 = s^3 E^4 - (s^3 + (p + 2\kappa q + 2\kappa)s^2)E^3 + \qquad (16)$$
$$((p + 2\kappa q + \kappa)s^2 + ((2\kappa q + \kappa)p + \kappa + (-\kappa q - \kappa)^2)s)E^2 -$$
$$((2\kappa qp + (\kappa q + \kappa)\kappa q)s + (\kappa q + \kappa)\kappa qp + \kappa^2 q)E + \kappa^2 q^2 p$$
$$= 0.$$

As indicated above, the concept of efficiency (parameter E) is convenient in developing the polynomial presented above as equation (16). However, one skilled in the art would recognize that a polynomial may be developed along the same lines but using a different independent variable, for example molar or reduced concentrations of target NA, $[s]_T$, or S, rather than E.

Chemical Model B: Two Parameter Chemical Model

A two parameter model was also developed for use in some embodiments of the present invention based on description of the chemical model above, with the additional simplification of treating $K_1 = \infty$. The simpler model is still necessarily recursive as it is not expressible in closed form, but the polynomial derived for this model (i.e., the polynomial analogous to equation (16) in the four parameter model) is a second degree polynomial in E with coefficients that are functions of two parameters (subscripts denoting cycle omitted for simplicity):

$$P_2 = s\,E_2 - (s+q+1)E + q = 0 \qquad (17)$$

Equation (17) is readily solved for E, $$E = \frac{s+q+1 - \sqrt{(s+q+1)^2 - 4sq}}{2s}. \qquad (18)$$

In this model, as $K_1 = \infty$, the reduced concentration, s (expressed as equation (15a) for the Chemical Model A above) is redefined as a function of the association constant $K_2$:

$$s = K_2 [s]_T \qquad (19)$$

As indicated above, the concept of efficiency (parameter E) is convenient in developing the polynomial presented above as equation (17). However, one skilled in the art would recognize that a polynomial may be developed along the same lines but using a different independent variable, for example molar or reduced concentrations of target NA, $[s]_T$, or S, rather than E.

Chemical Model A and Chemical Model B Objective Functions and Partial Derivatives The objective function for the recursive cycle chemistry models developed above and their partial derivatives are defined as follows. Partial derivatives of the objective functions are included here as they are necessary for most parameter estimation methods.

As described above, the general model described in equation (6a) can be considered as the sum of two models representing the background ($w_k$) and net signal ($y_k$), separately.

$$z_k = w_k + y_k \qquad (20a)$$
$$w_k = a + bk \qquad (20b)$$
$$y_k = Gx_o \prod_{i=1}^{k}(1 + E_i). \qquad (20c)$$

Both equations (20b) and (20c) can be written as recursions. The model for the background, $w_k$, becomes:

$$w_0 = a \qquad (21a)$$
$$w_1 = w_0 + b \qquad (21b)$$
$$w_k = w_{k-1} + b. \qquad (21c)$$

The model for the net signal, $y_n$, becomes:

$$y_0 = Gx_0 \qquad (22a)$$
$$y_1 = y_0(1+E_1) \qquad (22b)$$
$$y_k = y_{k-1}(1+E_k). \qquad (22c)$$

Because the background model is the same regardless of the cycle chemistry model, the derivatives of the background are easily developed as:

$$\frac{\partial w_o}{\partial a} = 1 \qquad (23a)$$
$$\frac{\partial w_i}{\partial a} = \frac{\partial w_0}{\partial a} = 1 \qquad (23b)$$
$$\frac{\partial w_k}{\partial a} = \frac{\partial w_{k-1}}{\partial a} = 1, \qquad (23c)$$

and $$\frac{\partial w_o}{\partial b} = 0 \qquad (24a)$$
$$\frac{\partial w_1}{\partial b} = \frac{\partial w_0}{\partial b} + 1 = 1 \qquad (24b)$$
$$\frac{\partial w_k}{\partial b} = \frac{\partial w_{k-1}}{\partial b} + 1 = k. \qquad (24c)$$

As the $Gx_0$ term in the net signal model is a product of a system composite factor and the initial target nucleic acid concentration, it is also independent of the cycle chemistry model used. Thus the partial derivatives with respect to $Gx_0$ are developed as follows:

$$\frac{\partial y_o}{\partial (Gx_o)} = 1 \qquad (25a)$$
$$\frac{\partial y_1}{\partial (Gx_o)} = \frac{\partial y_0}{\partial (Gx_o)}(1+E_1) \qquad (25b)$$
$$\frac{\partial y_k}{\partial (Gx_o)} = \frac{\partial y_{k-1}}{\partial y}(1+E_1) = \prod_{i=1}^{k}(1+E_i). \qquad (25c)$$

Chemical Model B Objective Function and Partial Derivatives

The two parameters in equation (18), $s_0$ and q, represent reduced target NA and reduced polymerase, respectively, in the PCR reaction. Reduced polymerase concentration, q, is constant in all cycles. The recursion for reduced target NA is developed as follows:

$$s_0 = \text{parameter to be estimated} \tag{26a}$$

$$s_1 = s_0 \tag{26b}$$

$$s_2 = s_1(1+E_1) \tag{26c}$$

$$s_k = s_{k-1}(1+E_{k-1}). \tag{26d}$$

The partial derivative $$\frac{\partial y_k}{\partial q}$$

is calculated recursively by the chain rule:

$$\frac{\partial y_1}{\partial q} = Gx_o \frac{\partial E_1}{\partial q} \tag{27a}$$

$$\frac{\partial y_k}{\partial q} = \frac{\partial y_{k-1}}{\partial q}(1+E_k) + y_{k-1}\frac{\partial E_k}{\partial q}. \tag{27b}$$

By implicitly differentiating equation (17)

$$\frac{\partial E_k}{\partial q}$$

is derived:

$$\frac{\partial E_k}{\partial q} = \frac{1-E_k}{1+s_k+q-2s_k E_k}. \tag{28}$$

The partial derivative $$\frac{\partial y_k}{\partial s_o}$$

also requires use of the chain rule:

$$\frac{\partial y_1}{\partial s_o} = Gx_o \frac{\partial E_1}{\partial s_1} \cdot \frac{\partial s_1}{\partial s_o} \tag{29a}$$

$$\frac{\partial y_2}{\partial s_o} = \frac{\partial y_1}{\partial s_o}(1+E_k) + y_1 \frac{\partial E_2}{\partial s_2} \cdot \frac{\partial s_2}{\partial s_1} \cdot \frac{\partial s_1}{\partial s_o} \tag{29b}$$

$$\frac{\partial y_k}{\partial s_o} = \frac{\partial y_{k-1}}{\partial s_o}(1+E_k) + y_{k-1} \frac{\partial E_k}{\partial s_k} \cdot \frac{\partial s_k}{\partial s_{k-1}} \cdot \ldots \cdot \frac{\partial s_1}{\partial s_o}. \tag{29c}$$

The partial derivative $$\frac{\partial s_k}{\partial s_{k-1}}$$

is obtained from equation (26d), $$\frac{\partial s_k}{\partial s_{k-1}} = 1 + E_{k-1} + s_{k-1}\frac{\partial E_{k-1}}{\partial s_{k-1}}. \tag{30}$$

Substituting equation (30) into equation (29c) reveals the general, recursive expression for the partial derivative $$\frac{\partial y_k}{\partial s_o}: \frac{\partial y_k}{\partial s_o} = \frac{\partial y_{k-1}}{\partial s_o}(1+E_k) + y_{k-1}\frac{\partial E_k}{\partial s_k}\prod_{i=1}^{k-1}\left[1+E_i+s_i\frac{\partial E_i}{\partial s_i}\right]. \tag{31}$$

The partial derivative $$\frac{\partial E_k}{\partial s_k}$$

may be obtained by implicit differentiation of equation (17):

$$\frac{\partial E_k}{\partial s_k} = \frac{E_k(1-E_k)}{1+s_k+q-2s_k E_k}. \tag{32}$$

Thus, in some embodiments of the present invention, $$\frac{\partial y_k}{\partial q}$$

may computed recursively from equations (27a-b) and (28), and $$\frac{\partial y_k}{\partial s_o}$$

may computed recursively from equations (29), (31), and (32).

Chemical Model A Objective Function and Partial Derivatives

Chemical model A extends chemical model B by including two additional parameters, $p_0$ and $\kappa$, representing initial reduced primer concentration and the ratio of the primer-template binding constant to the polymerase binding to primer-template duplex constant, respectively. The reduction in primer each cycle is represented by a recursion similar to equations (26a-d):

$$p_0 = \text{parameter to be estimated} \tag{33a}$$

$$p_1 = p_0 \tag{33b}$$

$$p_2 = p_1 - E_1 s_1 \tag{33c}$$

$$p_k = p_{k-1} - E_{k-1} s_{k-1} \tag{33d}$$

Two additional partial derivatives are needed over those in chemical model B. The partial derivative $$\frac{\partial y_k}{\partial \kappa}$$

is computed similarly to $$\frac{\partial y_k}{\partial q} : \frac{\partial y_1}{\partial \kappa} = G x_o \frac{\partial E_1}{\partial \kappa} \tag{34a}$$

$$\frac{\partial y_k}{\partial \kappa} = \frac{\partial y_{k-1}}{\partial \kappa}(1 + E_k) + y_{k-1} \frac{\partial E_k}{\partial \kappa}. \tag{34b}$$

The partial derivative $$\frac{\partial y_k}{\partial p_o}$$

is computed similarly to $$\frac{\partial y_k}{\partial s_o} : \frac{\partial y_k}{\partial p_o} = \frac{\partial y_{k-1}}{\partial p_o}(1 + E_k) + y_{k-1} \frac{\partial E_k}{\partial p_k} \prod_{i=1}^{k-1}\left[1 - s_i \frac{\partial E_i}{\partial p_i}\right], \tag{35a}$$

where the following equality is used:

$$\frac{\partial p_k}{\partial p_{k-1}} = 1 - s_{k-1} \frac{\partial E_{k-1}}{\partial p_{k-1}}. \tag{35b}$$

The partial derivatives of $y_k$ include partial derivatives of $E_k$ with respect to all of the parameters. These partial derivatives, obtained by implicit differentiation of equation (16), are all rational functions with the same denominator polynomial:

$$denom = s_k^2 E_k^4 - s_k^2(p_k + (2\kappa(1+q)) + s\kappa)E_k^3 + \tag{36}$$
$$s_k(\kappa(1 + \kappa(q+1)^2 + p_k(2q+1)) + s_k(p_k + \kappa(2q+1)))E_k^2 -$$
$$\kappa q(\kappa(p_k(q+1) + 1) + s_k(2p_k + \kappa(q+1)))E_k + \kappa^2 p_k q^2.$$

The four partial derivatives are;

$$\frac{\partial E_k}{\partial s_k} = [3s_k^2 E_k^3 - s_k(2(p_k + 2\kappa(1+q)) + 3s_k)E_k^2 + \tag{37a}$$
$$\kappa(1 + \kappa(q+1)^2 + p_k(2q+1) + (\kappa(4q+2) + 2p_k)s_k E_k -$$
$$\kappa q(2p_k + \kappa(q+1))](-E_k)/denom$$

$$\frac{\partial E_k}{\partial p_k} = [s_k^2 E_k^3 - s_k(s_k + \kappa(2q+1))E_k^2 + \tag{37b}$$
$$\kappa q(\kappa(q+1) + 2s_k)E_k - \kappa^2 q^2]/denom$$

$$\frac{\partial E_k}{\partial q} = [2s_k^2 E_k^3 - 2s_k(p_k + \kappa(1+q) + s_k)E_k^2 + \tag{37c}$$
$$(\kappa + \kappa(2q+1)p_k + (2p_k + \kappa(2q+1))s_k)E_k - 2\kappa p_k q]\kappa/denom$$

$$\frac{\partial E_k}{\partial \kappa} = [2s_k^2(q+1)E_k^3 - s_k((2q+1)p_k + 2\kappa(q+1)^2 + 1 + (2q+1)s_k) \tag{37d}$$
$$E_k^2 + 2q(\kappa(q+1)P_K + \kappa + (p_k + \kappa(q+1))s_k)$$
$$E_k - 2\kappa p_k q^2]/denom.$$

Polymerase Binding and Amplicon-Primer Competition Chemical Model

In yet other embodiments of the present invention, methods are based upon chemical models developed by extending the approach outlined above for chemical model A and chemical model B to account for amplicon-primer competition. Development of these extended models requires addition of a fourth reaction to the list of reactions in a PCR cycle as described as equations (7a-c) above:

$$s + s^* \rightleftharpoons d \tag{38}$$

$$K_4 = \frac{[d]}{[s][s^*]} = \frac{[d]}{[s]^2}$$

In equation (37), s* represents the strand complimentary to s, and d represents double-stranded NA. It is implicitly assumed that [s]=[s*]; thus $K_4$ may be represented solely in terms of [d] and [s]. This requires the conservation relation represented in equation (8a) to be rewritten as follows:

$$[s]_T = [s] + [h] + [r] + [d]. \tag{39}$$

The remaining conservation relations shown as equations (8b-c) are unchanged. As above, a subscripted $[\bullet]_T$ denotes a total concentration; absence of the subscript $_T$ denotes an equilibrium concentration. Integer subscripts on h and r are dropped as the reaction in equation (7c) (describing primer extension) is assumed to go to completion. That is, [r] denotes a concentration of duplex molecules with fully extended primers.

The recursions for $[s]_{T,k+1}$ and $[p]_{T,k+1}$ are the same as found in equations (10a-b) above.

Following the manipulations outlined above for the development of chemical model A, a model accounting for amplicon-primer competition (represented by equations (7a-c), (38), (39), (8b-c), and (10a-b)) was transformed to a form more easily implemented in a computer language by reducing to a single polynomial equation in cycle replication efficiency ($E_k=[r]_k/[s]_{T,k}$) with coefficients that are functions of reduced reactant concentrations. The equilibrium expressions in equations (7b) and (38) were solved for [h] and [d] and conservation relation in equation (8c) was solved for q to remove these quantities from the conservation relations for s and p:

$$[s]_T = [s] + \frac{[r]}{K_2([q]_T - [r])} + [r] + K_4[s]^2 \tag{40a}$$

$$[p]_T = [p] + \frac{[r]}{K_2([q]_T - [r])} + [r]. \tag{40b}$$

Thus, the number of parameters is reduced to five: three reduced concentrations (s, p, and q), and two ratios of association constants ($\kappa$, and D):

$$s = K_1[s]_T \tag{41a}$$

$$p = K_1[p]_T \tag{41b}$$

$$q = K_2[q]_T \tag{41c}$$

$$\kappa = K_1/K_2 \tag{41d}$$

$$D = K_4/K_1. \tag{41e}$$

With these parameters and the definition of efficiency found in equation (9c), the conservation relations for s and p (40a-b) are rewritten as:

$$s = K_1[s] + \frac{\kappa Es}{\kappa q - Es} + Es + DK_1^2[s]^2 \tag{42a}$$

$$p = K_1[p] + \frac{\kappa Es}{\kappa q - Es} + Es. \tag{42b}$$

$$q = K_2[q] + \frac{Es}{\kappa}. \tag{42c}$$

Multiplying the first two equilibrium expressions in equations (7a-b), substituting Es for [r], and rearranging the resulting equation yields:

$$Es = K_1[s]K_1[p]K_2[q]. \tag{43}$$

Equations (42b-c) were solved for $K_1[p]$ and $K_2[q]$, with the results substituted into equation (43), and solved for $K_1[s]$. This result is substituted into equation (42a) and rearranged to reduce the model to a single equation:

$$[(1-E)(\kappa q - Es) - \kappa E][(p - Es)(\kappa q - Es) - \kappa Es]^2 - \tag{44}$$
$$\kappa E(\kappa q - Es)[(p - Es)(\kappa q - Es) - \kappa Es] - \kappa^2 E^2 Ds(\kappa q - Es) = 0$$

which expands to a sixth degree polynomial in E, $$P_6 = s^5 E^6 - (s^5 + (3\kappa q + 3\kappa + 2p)s^4)E^5 + ((3\kappa q + 2p + 2\kappa)s4 + \tag{45}$$
$$(p2 + (6\kappa q + 4\kappa)p + 3\kappa^2 q^2 + 6\kappa^2 q + \kappa + 3\kappa^2)s^3)E^4 -$$
$$((p^2 + (6\kappa q + 2\kappa)p + 3\kappa^2 q^2 + 4\kappa^2 q + \kappa^2)s^3 +$$
$$((3\kappa q + \kappa)p^2 + (6\kappa^2 q^2 + 8\kappa^2 q + \kappa + 2\kappa^2)$$
$$p + \kappa^3 q^3 + 3\kappa^3 q^2 + 2\kappa^2 + 3\kappa^3)q + \kappa^3 +$$
$$(1 - D)\kappa^2)s^2)E^3 + ((3\kappa q p^2 + (6\kappa^2 q^2 + 4\kappa^2 q)p +$$
$$\kappa^3 q^3 + 2\kappa^3 q^2 + \kappa^3 q)s^2 + ((3\kappa^2 q^2 + 2\kappa^2 q)p^2 +$$
$$(2\kappa^3 q^3 + 4\kappa^3 q^2 + (2\kappa^2 + 2\kappa^3)q)p + \kappa^3 q^2 +$$
$$(1 - D)\kappa^3 q)s)E^2 - ((3p^2 \kappa^2 q^2 + (2\kappa^3 q^3 + 2\kappa^3 q^2)p)s +$$
$$(\kappa^3 q^3 + \kappa^3 q^2)p^2 + \kappa^3 q^2 p)E + \kappa^3 q^3 p^2 = 0.$$

Note that, as in chemical model A and chemical model B described above, E is not itself a model parameter but is computed as a root of $P_6$ whose coefficients are functions of the five parameters s, p, q, κ, and D.

As indicated above, the concept of efficiency (parameter E) is convenient in developing the polynomial presented above as equation (45). However, one skilled in the art would recognize that a polynomial may be developed along the same lines but using a different independent variable, for example molar or reduced concentrations of target NA, $[s]_T$, or S, rather than E.

Chemical Model C: Simplified Polymerase Binding and Amplicon-Primer Competition Chemical Model The above developed polymerase binding and amplicon competition chemical model can be simplified somewhat by adding the assumption that $[p]_T$ is sufficiently large that $[p] \approx [p]_T$. This idealization reduces the number of model parameters by two. From the equilibrium expressions in equations (7a-b) and the conservation relations in equations (39) and (8b-c), the following two equations can be developed:

$$[s] = \frac{[r]}{K_1[p]_T K_2([q]_T - [r])} \tag{46a}$$

$$K_2[s]_T = K_2[s] + \frac{K_2[r]}{K_2([q]_T - [r])} + K_2[r] + K_2 K_4[s]^2. \tag{46b}$$

Applying the same definition of efficiency found in equation (9c), but defining new reduced concentration parameters, $$s = K_2[s]_T \tag{47a}$$

$$q = K_2[q]_T \tag{47b}$$

$$D = \frac{K_4}{K_2(K_1[p]_T)^2}, \tag{47c}$$

equations (46a-b) are reduced to a single equation, $$\frac{K_4}{K_2(K_1[p]_T)^2} sE^2 + \left(1 + \frac{1}{K_1[p]_T}\right)(q - Es)E - (1-E)(q-Es)^2. \tag{48}$$

Noting that $K_1[p]_T \gg 1$ and substituting D (as defined in equation (47c)) into equation (48) effects a simplification, $$DsE^2 + (q-Es)E - (1-E)(q-Es)^2 = 0, \tag{49}$$

which expands into a cubic polynomial in E, $$P_3 = s^2 E^3 - (s^2 + (1 - D + 2q)s)E^2 + q(2s + q + 1)E - q^2 = 0 \tag{50}$$

As above, note that E is not itself a model parameter, but is computed as a root of $P_3$ in equation (50) whose coefficients are functions of the three redefined parameters s, q, and D (as defined in equations (47a-c)).

As indicated above, the concept of efficiency (parameter E) is convenient in developing the polynomial presented above as equation (50). However, one skilled in the art would recognize that a polynomial may be developed along the same lines but using a different independent variable, for example molar or reduced concentrations of target NA, $[s]_T$, or S, rather than E.

Chemical Model C Objective Function and Partial Derivatives

The objective function for chemical model C is the same as all of the models described above expressing $y_k$ as a function of the initial target NA amount $x_0$, the system factor G, and the replication efficiency in each cycle, $E_i$:

$$y_k = Gx_0 \prod_{i=2}^{k} (1 + E_i) \tag{51}$$

In this model, net signal $y_k$ is computed recursively:

$$y_0 = Gx_0 \tag{52a}$$

$$y_1 = y_0(1+E_1) \tag{52b}$$

$$y_k = y_{k-1}(1+E_k). \tag{52c}$$

From the polynomial in equation (50), it is apparent that E depends on three parameters: $s_k$, q, and D. The later two are constant through all cycles, and the first is determined as a recursion beginning with $s_0$, the total reduced target NA in the sample:

$$s_0 = \text{parameter to be estimated} \tag{53a}$$

$$s_1 = s_0 \tag{53b}$$

$$s_2 = s_1(1+E_1) \tag{53c}$$

$$s_k = s_{k-1}(1+E_{k-1}) \tag{53d}$$

Implementation of chemical model C differs from chemical models A and B in that in chemical models A and B, $s_0$ is a model parameter that is estimated during the modeling process. However, in chemical model C, $s_0$ is separated into two factors:

$$s_o = x_o \frac{K_2}{NV} = x_o K, \tag{54}$$

where N represents Avogadro's constant, V denotes the reaction volume, $K_2$ is defined above, and K is defined to represent the composite quantity $$\frac{K_2}{NV}.$$

Similarly to the term $Gx_0$ in chemical models A and B, one of K and $x_0$ will be an estimated parameter. Which of these two parameters is estimated depends on whether data generated from calibrator or test samples are being analyzed.

It is possible to estimate parameter values by a nonlinear least squares procedure using a general numerical method for computing partial derivatives of equations (52a-c), however in most cases programming (or using) analytic derivatives is more efficient computationally. The partial derivatives necessary for most parameter estimation methods are computed analytically:

$$\frac{\partial y_k}{\partial G} = x_o \prod_{i=1}^{k} (1+E_i) = y_k/G \tag{55}$$

The derivative $$\frac{\partial y_k}{\partial q}$$

is obtained recursively from equation (52a-c):

$$\frac{\partial y_1}{\partial q} = Gx_o \frac{\partial E_1}{\partial q} \tag{56a}$$

$$\frac{\partial y_k}{\partial q} = \frac{\partial y_{k-1}}{\partial q}(1+E_k) + y_{k-1}\frac{\partial E_k}{\partial q} \tag{56b}$$

The partial derivative is obtained by implicitly differentiating equation (50):

$$\frac{\partial E_k}{\partial q} = [2sE_k^2 - (2(s+q)+1)E_k + 2q]/denom, \tag{57a}$$

with $$denom = 3s^2 E_k^2 - (2s^2 + 2(q+1-D)s)E_k + q(2s+q+1). \tag{57b}$$

The partial derivative with respect to D is similarly obtained:

$$\frac{\partial y_1}{\partial D} = Gx_o \frac{\partial E_1}{\partial D} \tag{58a}$$

$$\frac{\partial y_k}{\partial D} = \frac{\partial y_{k-1}}{\partial D}(1+E_k) + y_{k-1}\frac{\partial E_k}{\partial D}, \tag{58b}$$

and $$\frac{\partial E_k}{\partial D} = -sE_k^2/denom. \tag{58c}$$

The partial derivatives $$\frac{\partial y_k}{\partial x_o} \text{ and } \frac{\partial y_k}{\partial K}$$

are also computed recursively:

$$\frac{\partial y_1}{\partial x_o} = G(1+E_1) + Gx_o \frac{\partial E_1}{\partial x_o} \tag{59a}$$

$$\frac{\partial y_k}{\partial x_o} = \frac{\partial y_{k-1}}{\partial x_o}(1+E_k) + y_{k-1}\frac{\partial E_k}{\partial x_o} \tag{59b}$$

and $$\frac{\partial y_1}{\partial K} = Gx_o \frac{\partial E_1}{\partial K} \tag{60a}$$

$$\frac{\partial y_k}{\partial K} = \frac{\partial y_{k-1}}{\partial K}(1+E_k) + y_{k-1}\frac{\partial E_k}{\partial K}. \tag{60b}$$

Additional application of the chain rule, $$\frac{\partial E_k}{\partial x_o} = K\frac{\partial E_k}{\partial s_o} \tag{61a}$$

$$\frac{\partial E_k}{\partial K} = x_o\frac{\partial E_k}{\partial s_o}, \tag{61b}$$

allows expression of equations (59a-b) and (60a-b) in terms of partial derivatives with respect to $s_0$, computed similarly to those in equations (34b) and (31).

$$\frac{\partial y_1}{\partial x_o} = G(1+E_1) + GKx_o\frac{\partial E_1}{\partial s_o} \tag{62a}$$

$$\frac{\partial y_k}{\partial x_o} = \frac{\partial y_{k-1}}{\partial x_o}(1+E_k) + y_{k-1}K\frac{\partial E_k}{\partial s_k}\prod_{i=1}^{k-1}\left[1 + E_i + s_i\frac{\partial E_i}{\partial s_i}\right] \tag{62b}$$

and $$\frac{\partial y_1}{\partial K} = Gx_o\frac{\partial E_1}{\partial s_o} \tag{63a}$$

-continued $$\frac{\partial y_k}{\partial K} = \frac{\partial y_{k-1}}{\partial K}(1+E_k) + y_{k-1}x_o\frac{\partial E_k}{\partial s_k}\prod_{i=1}^{k-1}\left[1+E_i+s_i\frac{\partial E_i}{\partial s_i}\right]$$ (63b)

Finally, implicit differentiation of equation (50) can be used to obtain the partial derivative of efficiency with respect to reduced target amount, $$\frac{\partial E_k}{\partial s_k} = E_k[2sE_k^2 - (2(s+q)+1-D)E_k + 2q]/denom.$$ (64)

Implementation of Chemical Model A or Chemical Model B

Implementation of an embodiment of the present invention utilizing chemical model A or chemical model B begins by identifying the PCR cycle where efficiency was greatest, and from that point defining the subset of cycles to be analyzed. Equation (6a) is applicable to raw data for a range of cycles beginning before replication is apparent and ending at a cycle where $E_k$ has decreased to a predetermined absolute lower limit or a relative amount from the peak efficiency. For example, the ending cycle may have an efficiency within the range of 10% to 50%, inclusive, of the peak efficiency. In embodiments of the present invention utilizing either chemical model A or chemical model B, the efficiency of the selected ending cycle is preferably within the range of 10% to 35%, inclusive, of peak efficiency; preferably within the range of 15 to 30%, inclusive, of peak efficiency; preferably within the range of 20% to 25%, inclusive, of peak efficiency; preferably about 20% of peak efficiency. In alternative embodiments, an absolute efficiency cut-off is used. In these embodiments, the selected ending cycle has an efficiency that is some predetermined percentage of the theoretical maximum of 100%; preferably, the selected ending cycle has an absolute efficiency within the range of 10% to 50%, inclusive; preferably within the range of 10% to 35%, inclusive; preferably within the range of 15 to 30%, inclusive; preferably within the range of 20 to 25%, inclusive; preferably about 20%. The ending cycle may be determined empirically by goodness of fit of the model, or precision of parameter estimates. In all embodiments, the subset of cycles to be analyzed comprises the ending cycle and a number of cycles immediately preceding; preferably totaling 5 to 15 cycles; more preferably, the subset of cycles to be analyzed comprises the ending cycle and the preceding nine cycles. The raw data for cycles within the subset may then be normalized to give a signal range from zero to one.

Equation (6b) is applicable to raw data for a range of cycles beginning before replication is apparent and ending at a cycle where the ratio $x_i/x_{i-1}$ approaches a predefined value.

Preferably, parameters of the combined PCR/background model from equations (6a) and (6b) and parameters of a chemical model, such as chemical model A or B, may then be estimated to fit the data in the subset of cycles analyzed by any suitable method known in the art. Parameters may be estimated by the Levenberg-Marquardt nonlinear minimization algorithm which utilizes nonlinear least squares (NLLS) curve fitting. However, other suitable methods of deriving parameter estimates may include methods such as maximum likelihood (ML) or Bayesian methods.

Regardless of estimation method employed, nonlinear parameter estimation methods generally require starting estimates for the parameters. Estimates for the parameters G, $x_0$, and $s_0$ are made by temporarily treating an early subset of the data as adequately represented by a constant efficiency model. In this case, a first estimate of efficiency E can be made from the net data, $y_k$:

$$E_o = \max\left[\frac{y_{k-1}+y_k+y_{k+1}}{y_{k-2}+y_{k-1}+y_k}-1\right].$$ (65a)

Letting $k_{max}$ denote the cycle index corresponding to $E_0$, the quantity $Gx_0$ is estimated as:

$$Gx_0 = y_{k\,max}(1+E_0)^{-k_{max}}.$$ (65b)

For calibration samples, $x_0$ is known, and G is estimated from the quantity $Gx_0$ estimated in equation (65b) and the known quantity of $x_0$ by: $G=Gx_0/x_0$. For test samples (with unknown $x_0$) G is known, and $x_0$ is estimated from the quantity $Gx_0$ (estimated in equation (65b)) and the known quantity of G by: $x_0=Gx_0/G$. With an estimated value for $x_0$, an estimate for $s_0$ is obtained from formulas (69) or (70) by assuming values of $10^9$ or $10^7$ for $K_1$ or $K_2$, respectively, and applying the known reaction volume, V.

Two assumed initial reduced concentrations (primer $p_0=100$, and polymerase $q_0=20$) are justified by standard practice in PCR. Additionally, the association constant for primer binding to template is assumed to be much greater than for polymerase binding to template-primer complex ($\kappa=100$). With these starting values, the polynomial of the chemical model employed (preferably chemical models A, B, C, or the polymerase binding amplicon-primer competition model) may be solved for E by any method known in the art. For example, a polynomial may be solved for E by Newton root-finding (restricting the domain to [0, 1]) and solving for the smallest root. Thus, E is not itself a parameter derived by the above described NLLS estimation.

Initial estimates for the background parameters a and b from equation (6a) or (6b) are readily made from early cycles before replication is apparent, for example typically cycles 3-8, and can be derived by any method known in the art. These initial estimates may then be used in the combined modeling of the general PCR/background model in equation (6a) or (6b), and a chemical model, such as chemical model A or B.

Alternatively, the background parameters in equation (6a) or (6b) may be estimated separately from the chemical model parameters in a pre-analysis step. Implemented in this way, a constant efficiency geometric growth model may be assumed in the pre-analysis to estimate by NLLS the background parameters a and b along with the parameters c and $E_c$:

$$z_k = a+bk+c(1+E_c)^k$$ (67)

An estimate of a constant amplification efficiency, $E_c$, may be developed from the ratio of a 3-point moving average offset by one cycle. That is, representing the conditioned data as $y_k$, the estimate of $E_c$ may be computed as:

$$E_c = \max\left[\frac{y_{k-1}+y_k+y_{k+1}}{y_{k-2}+y_{k-1}+y_k}-1\right]$$ (68)

It is important to note that the constant amplification efficiency, $E_c$, is only used in the pre-analysis determination of background parameters in equation (67). In the chemical models of the present invention, amplification efficiency is not constant.

Implementation of Chemical Model C

In some embodiments utilizing chemical model C, the selected ending cycle has an efficiency that is some predetermined percentage of the peak efficiency; preferably between 10 and 50%; preferably between 20% and 40% of the peak efficiency; preferably about 30% of the peak efficiency. In preferred embodiments, an absolute efficiency cut-off is used. In these embodiments, the selected ending cycle has an efficiency that is some predetermined percentage of the theoretical maximum of 100%; preferably, the selected ending cycle has an absolute efficiency between 10% and 50%; preferably between 20% and 40%; preferably about 30%. Selection of a subset for analysis from a single profile is demonstrated in FIG. 2 and discussed in detail in Example 1, below.

The preferred implementation of chemical model C differs from the implementation of chemical models A and B in that the alternative method described above (i.e., separate estimation of background parameters in a pre-analysis step) is preferred. This is because estimating parameters representing amplicon competition is more effective when multiple samples with known target NA amounts (i.e., calibrators) are analyzed. In modeling calibrators, the objective function is preferably applied to selected subsequences of cycles from multiple profiles at once, rather than a subset of cycles from a single profile. This approach has the advantage that parameters representing system gain and binding constants, which are theoretically the same for all samples, are only estimated once for all profiles rather for each profile independently. However, this approach still necessitates estimation of background parameters individually for each sample, as background parameters may be different for each sample.

Estimation of Initial Target NA from Estimated Parameters

One feature of some embodiments of the present invention is that two independent means of estimating the initial amount of target NA in a sample are provided by the models described above. First, initial target NA, $x_0$, may be directly solved from the modeling of equation (6a) or (6b).

Second, as defined in equations (15a) and (19), the $s_0$ parameter is directly proportional to the amount of initial target NA, with the proportionality factor being an association constant, $K_1$ or $K_2$ depending on the chemical model, divided by Avogadro's number (N) times the sample volume (V):

$$s_o = x_o \frac{K_1}{NV} \quad (69)$$

$$s_o = x_o \frac{K_2}{NV} \quad (70)$$

Some embodiments of the present invention provide a target NA estimation apparatus comprising a generic or specialized computer or another suitable logic device, such as a microprocessor or ASIC configured to execute processes, such as software methods or other computer-readable instructions. Referring now to FIG. 1, an exemplary device for implementation of a target NA estimation method in accordance with embodiments of the present invention is schematically illustrated. The target NA estimation device 100 includes a processor 110 configured to execute a process, such as a software method or other computer-readable instructions. The processor 110 is coupled to an input module 120 configured to receive input from a user or device. The user may input data using, for example, a keyboard or other input interface. A device for inputting data may be, for example, an analytical instrument, such as a PCR system for generating fluorescence data indicative of amount of target NA present in a sample.

The processor 110 is also coupled to an output module 130 configured to output information to a user. In various embodiments, the output module 130 is configured to output information through a screen, monitor, printer, or means for writing computer readable information to a recordable media, or other means.

The target NA estimation apparatus 100 also includes a memory unit 140 coupled to the processor 110. The memory unit 140 may be configured to store data, software applications, or other such information. In one embodiment, the memory unit 140 has a program product stored thereon, and the processor 110 may access the program product to execute the program product.

In related embodiments, the computer or logic device may be attached to a display apparatus, such as a display monitor, to display the results of the calculations, and/or attached a means for writing results of the calculations to a recordable media. In these embodiments, results of the QPCR data analysis may be accessed by the operator.

The present invention finds applications in a number of different fields, including assays, investigating differences in gene expression, gene quantitation, genotyping, investigation of mutations, gene therapy, investigation of viral and bacterial loadings, and indeed any type of quantitative PCR analysis. For example, the disclosed methods may be used to qualitatively assess the presence of target NA, which itself may be indicative of a disease state or condition, particularly to qualitatively assess the presence of an infectious agent (either viral or bacterial) in any clinical sample type suitable for PCR amplification.

As seen in the following examples, methods which utilize the phenomenological model in equation (6a) or (6b) in concert with either chemical model B (using $s_0$), or chemical model C are preferred. The inventors suspect that the relative increase in inaccuracy demonstrated by the phenomenological model in equation (6a) or (6b) in concert with chemical model A may result from the NLLS method used to estimate model parameters, which may be finding local, rather than global, minima, thus leading to inaccuracies in the estimated amounts of initial target NA. Chemical models B and C, which have fewer parameters to estimate, may be less susceptible to such influences. The following examples demonstrate that estimations of the amount of initial target NA by the methods herein are accurate across a wide range, down to at least about 1000 copies/µl. For some assays, this range may extend to even lower levels of copies/µl, and be more accurate than obtainable by other methods.

In the specific examples discussed below, methods of the present invent were utilized to analyze fluorescence signal obtained from QPCR analysis. However, the above description of the present invention and the examples discussed below are not intended to limit the general applicability of the invention as a whole. For example, signals other than fluorescence signal obtained from fluorescent dye can be used as basis for the analysis, as long as the signal is representative of the amount of amplicon.

EXAMPLES

Example 1

Subset of Cycles to be Analyzed

Figure 2:
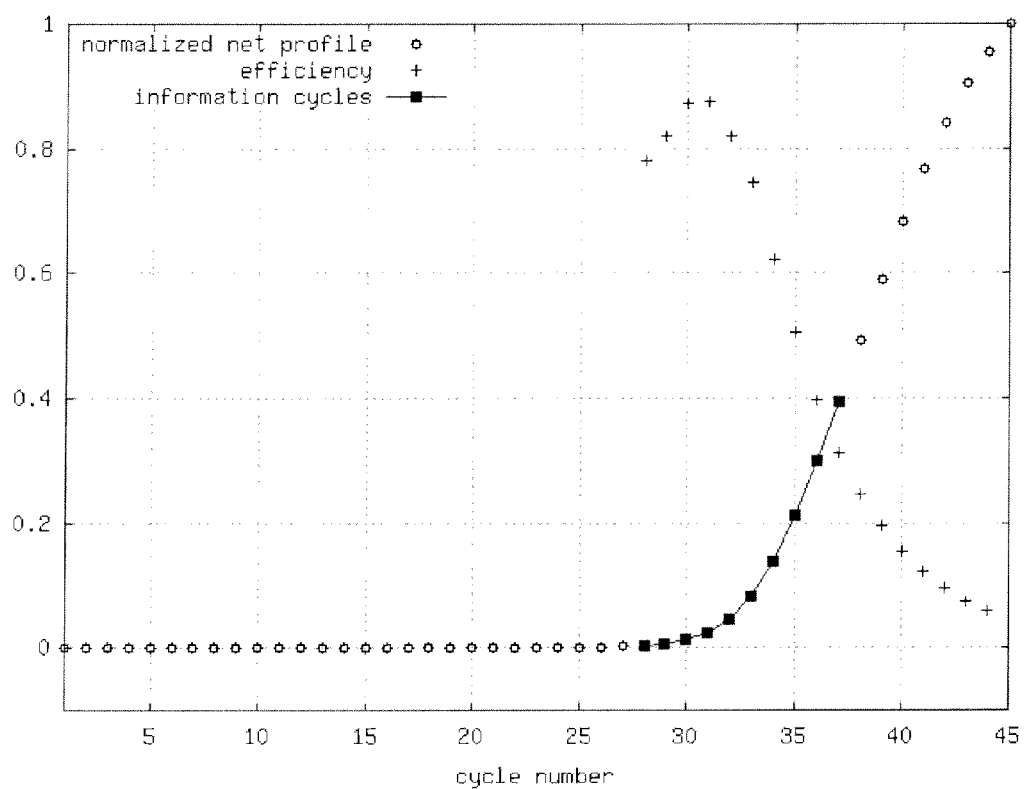
FIG. 2 shows selection of a subset of PCR data for analysis from a single profile. Specifics are discussed in detail in Example 1.

As can be seen in the exemplary profile demonstrated in FIG. 2, the peak amplification efficiency occurs at cycle 31. The amplification efficiency for this cycle is approximately 0.85, and from this point forward, the amplification efficiency decreases. The final cycle of the subset to be analyzed is the last cycle with amplification efficiency exceeding a preselected amplification efficiency limit. In this example, the final cycle is selected to be the last cycle with absolute amplification efficiency exceeding 30%. As seen in FIG. 2, cycles after cycle 37 demonstrate less than 30% absolute efficiency. Thus, cycle 38 is selected as the final cycle in the subset to be analyzed.

The subset of cycles to be analyzed is then defined as the final cycle and some number of preceding cycles. As seen in FIG. 2, nine preceding cycles have been selected to complete the subset of cycles to be analyzed in this example, giving a subset of cycles 28-37.

Example 2

Quantitation Dynamic Range and Linearity Studies

Genomic DNA was isolated from Varicella Zoster Virus (VZV, ATCC VR-1367) using a QiaAmp viral RNA manual kit (Qiagen). The isolated DNA was diluted in a buffer composed of Tris and EDTA (commonly known as TE buffer) to generate a 10-E2, 10-E3, 10-E4, 10-E5, 10-E6, 10-E7, and 10-E8 folds dilution series. The diluted DNA samples were amplified by Simplexa VZV real-time PCR assay on ABI7500 system (Applied Biotechnologies, Inc.).

The Simplexa VZV real-time PCR assay used a primer mix containing VZV and internal control (IC) primer pairs. The concentration is 3000 nM for VZV primer pair and 1000 nM for IC primer in the primer mix. The sequences of the primers were listed in the Table 1.

TABLE 1

| VZV and internal control (IC) sequences | |
|---|---|
| VZV Dx2 Scorpion™ | Quencher-AGCGGAGTGAAACGGTACAAACTCCGCT (SEQ ID NO: 1) -FAM-GTTATTGTTTACGCTTCCCGCTGAA (SEQ ID NO: 2) |
| VZV Reverse | GCCCGTTTGCTTACTCTGGATAA (SEQ ID NO: 3) |
| IC Dx2 Scorpion™ | Quencher-TGCGAACTGGCAAGCT (SEQ ID NO: 4) -CFR610-ATTCGCCCTTTGTTTCGACCTA (SEQ ID NO: 5) |
| IC Reverse | CCGACGACTGACGAGCAA (SEQ ID NO: 6) |

The assay used a master mix containing enzymes, buffers, and dNTPs assembled according to Table 2.

TABLE 2

| Master Mix Composition | | |
|---|---|---|
| Component | Master Mix Concentration | Final Reaction Concentration |
| Tris-HCl, pH 8.3 | 100 mM | 50 nM |
| MgCl$_2$ | 5 mM | 2.5 mM |
| KCl | 20 nM | 10 nM |
| (NH$_4$)$_2$SO$_4$ | 10 mM | 10 mM |
| dNTPs (U, A, G, C) | 400 μM | 200 μM |
| FastStart DNA Polymerase (Roche) | 4 U | 2 U |

PCR reactions consisted of 12.5 μL master mix, 2.5 μL primer mix, 10.0 μL sample or control to make 25.0 μL (see Table 3). Master mix, and primer mix were added in a template-free room; sample or control was added in a template-allowed room.

TABLE 3

| Amplification Reaction Mix | |
|---|---|
| Component | Volume (μL) |
| Master Mix | 12.5 |
| Primer Mix | 2.5 |
| Sample or Control | 10 |
| Total | 25 |

Amplification was carried out in an ABI7500 real-time PCR instrument (Applied Biosystems Inc., Foster City, Calif.) with the thermal program of 95° C. for 10 min for one cycle, 95° C. for 15 sec and 60° C. for 35 sec for 45 cycles. VZV signal (FAM) was collected from channel A, and IC signal (CFR610) was collected from channel D on the ABI7500 real-time PCR instrument. Signal intensity data was collected for eight replicates of each diluted DNA sample.

The dilution series was used to demonstrate the linearity of amounts of initial target NA estimated by methods of the instant invention utilizing the phenomenological model in equation (6a) in concert with chemical model A (P/A Method), chemical model B (P/B Method), and chemical model C (P/C Method). For comparison, signal intensity data was also analyzed by the threshold (Ct) standard curve method (the Threshold Method).

Data from the resulting analysis by the Threshold Method, the P/B Method with initial target NA derived from the $s_0$ parameter, and the P/C Method are shown below in Table 4.

TABLE 4

Results of estimation by Threshold Method, the P/B Method (using the $s_o$ parameter), and the P/C Method

| Actual Initial Target NA | Threshold Method | | | P/B Method (from $s_o$) | | | P/C Method | | |
|---|---|---|---|---|---|---|---|---|---|
| | Mean Predicted Value | Error (%) | CV (%) | Mean Predicted Value | Error (%) | CV (%) | Mean Predicted Value | Error (%) | CV (%) |
| 100000000 | 120288232 | 20 | 5 | 126983479 | 27 | 19 | 117120050 | 17 | 8 |
| 10000000 | 10827560 | 8 | 5 | 9120602 | −9 | 9 | 9042280 | −10 | 7 |
| 1000000 | 987247 | −1 | 5 | 951029 | −5 | 28 | 881304 | −12 | 7 |
| 100000 | 91813 | −8 | 12 | 88071 | −12 | 17 | 94626 | −5 | 13 |
| 10000 | 8307 | −17 | 7 | 8827 | −12 | 9 | 9839 | −2 | 4 |
| 1000 | 830 | −17 | 32 | 1111 | 11 | 10 | 1104 | 10 | 14 |
| 100 | 78 | −22 | 36 | 122 | 22 | 47 | 124 | 24 | 47 |

Figure 3:
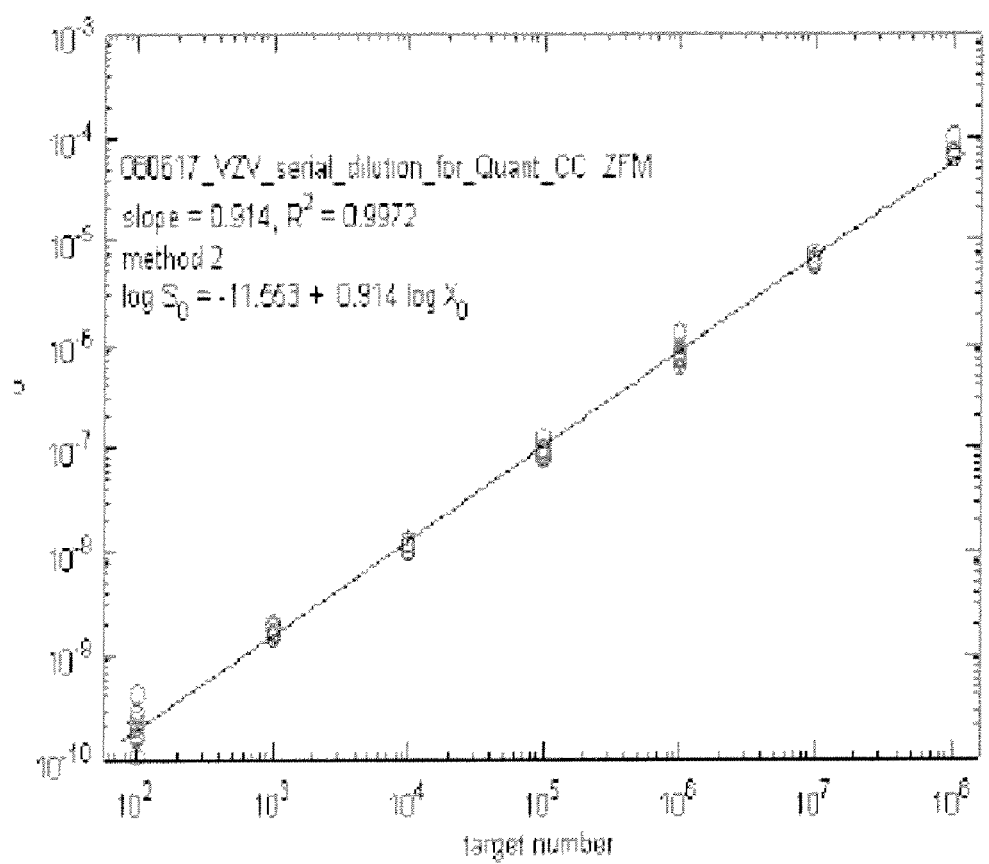
FIGS. 3 and 4 show dynamic range and linearity of QPCR data analysis by an embodiment of the present invention utilizing a two parameter chemical model ($s_0$), and an embodiment of the present invention utilizing a polymerase binding amplicon competition chemical model, respectively, for samples containing genomic DNA isolated from Varicella Zoster Virus. Details are discussed in Example 2.
Figure 4:
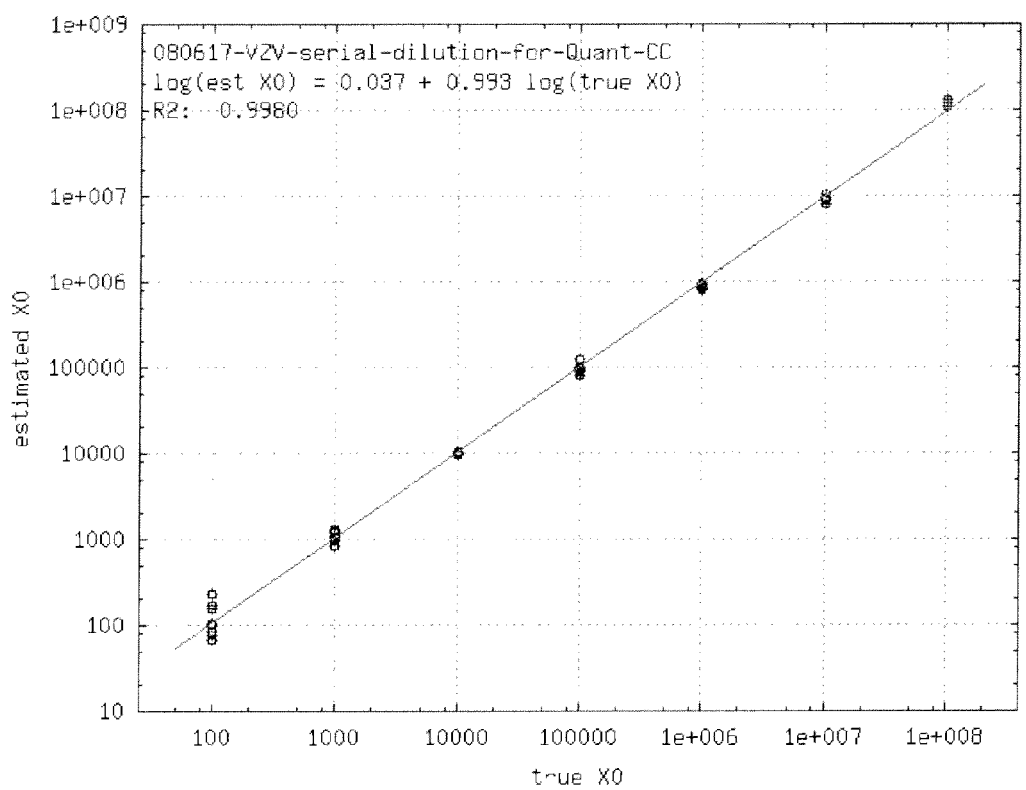

Plots of the linearity of amount of initial target NA estimated by the P/B Method (from $s_0$) and the P/C Method are shown in FIGS. 3 and 4, respectively. As FIG. 4 demonstrates, the P/B Method for estimating initial target NA from $s_0$ demonstrates linearity across six orders of magnitude.

Figure 5:
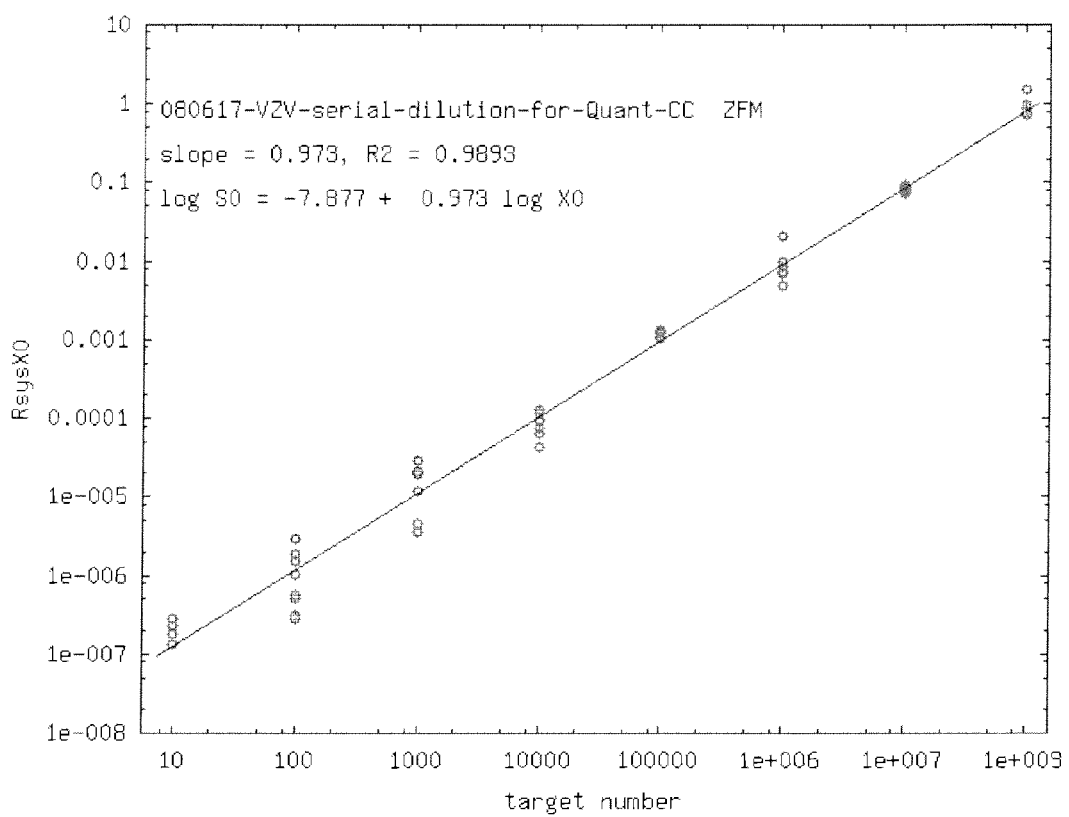
FIGS. 5 and 6 show dynamic range and linearity of QPCR data analysis by an embodiment of the present invention utilizing a four parameter chemical model ($Gx_0$), and an embodiment of the present invention utilizing a two parameter chemical model ($Gx_0$), respectively, for samples containing genomic DNA isolated from Varicella Zoster Virus. Details are discussed in Example 2.
Figure 6:
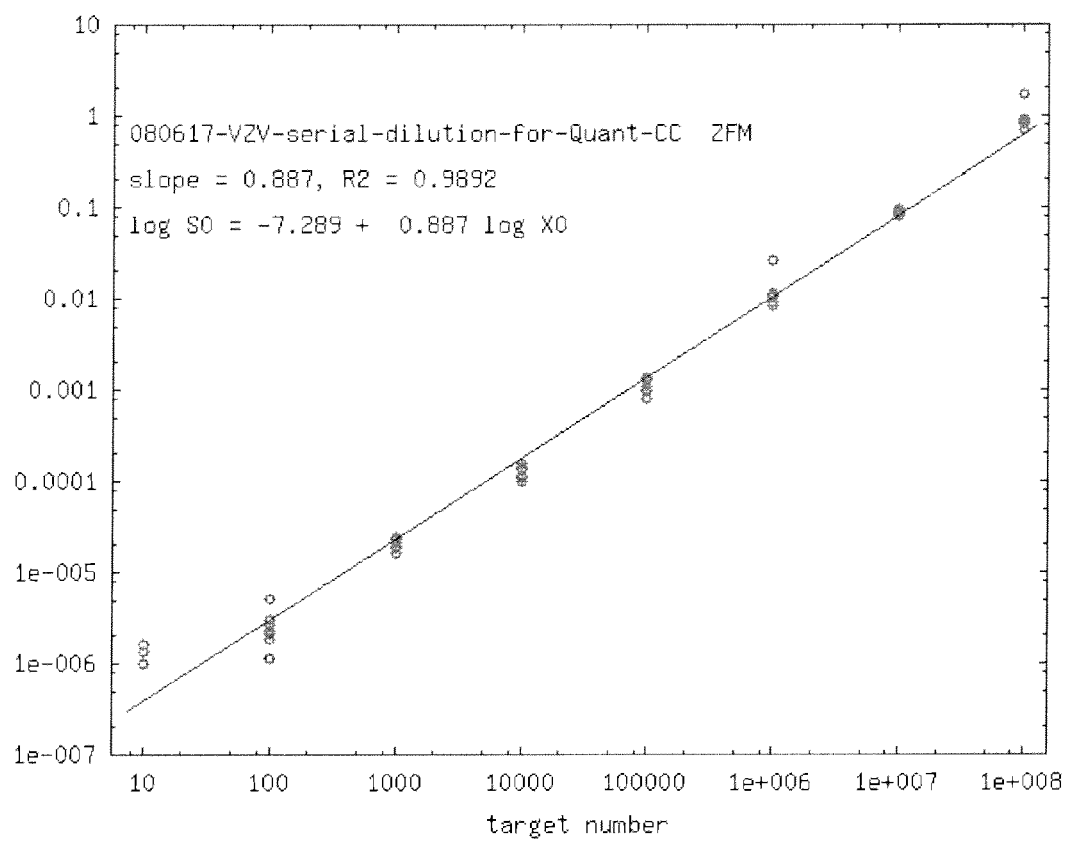

Amount of initial target NA was also estimated with the P/A Method (from $Gx_0$) and the P/B Method (from $Gx_0$). Data resulting from these estimations are shown in Table 5. Plots of the linearity of amount of initial target NA estimated by the P/A Method (from $Gx_0$) and the P/B Method (from $Gx_0$) are shown in FIGS. 5 and 6, respectively.

TABLE 5

Results of estimation by P/B Method and P/A Method, both using the $Gx_o$ parameter

| Actual Initial Target NA | P/A Method (from $Gx_o$) | | | P/B Method (from $Gx_o$) | | |
|---|---|---|---|---|---|---|
| | Mean Predicted Value | Error (%) | CV (%) | Mean Predicted Value | Error (%) | CV (%) |
| 100000000 | 104575619 | 5 | 30 | 123582684 | 23 | 37 |
| 10000000 | 9036335 | −10 | 8 | 9642491 | −4 | 7 |
| 1000000 | 1032696 | 3 | 53 | 1109437 | 11 | 58 |
| 100000 | 125534 | 26 | 11 | 85512 | −15 | 20 |
| 10000 | 9055 | −10 | 32 | 8090 | −19 | 17 |
| 1000 | 1672 | 67 | 54 | 1130 | 13 | 14 |
| 100 | 110 | 10 | 84 | 127 | 27 | 47 |

The linearity demonstrated by the Threshold Method was very comparable to that demonstrated by the P/A, P/B, and P/C methods.

Example 3

Quantitation for Cytomegalovirus (CMV) DNA

Quantified CMV (strain AD169) genomic DNA (Advanced Biotechnologies, Inc.) was diluted in TE buffer to 5, 50, 500, 5,000, and 50,000 copies/reaction. The diluted DNA samples were amplified by Simplexa CMV real-time PCR assay on ABI7500 system (Applied Biosystems, Inc.).

The Simplexa CMV real-time PCR assay used a primer mix containing CMV and internal control (IC) primer pairs. The concentration is 5000 nM for the CMV primer pair and 1000 nM for the IC primer pair in the primer mix. The sequences of the primer were listed in the Table 6.

TABLE 6

CMV and IC sequences

| | |
|---|---|
| CMVUL11M5 Scorpion™ | Quencher-aggcgtgCAGCACCAACACGTGGCTACA-CACGCCT (SEQ ID NO: 7) -FAM-TAACGATTACGACCGCTAAAACC (SEQ ID NO: 8) |
| CMVUL11R1 Reverse | CAGCGGAAACACCGTTACAA (SEQ ID NO: 9) |
| IC Dx2 Scorpion™ | Quencher-TGCGAACTGGCAAGCT (SEQ ID NO: 4) -Q670-ATTCGCCCTTTGTTTCGACCTA (SEQ ID NO: 5) |
| IC Reverse | CCGACGACTGACGAGCAA (SEQ ID NO: 6) |

PCR reactions consisted of the same as described in Example 2.

Amplification was carried out by the same method and instrument as described in Example 2. CMV signal (FAM) was collected from channel A, and IC signal (Q670) was collected from channel E on the ABI7500 real-time PCR instrument. Signal intensity data was collected for six replicates of each diluted DNA sample.

The dilution series was used to demonstrate the linearity of amounts of initial target NA estimated by the P/B Method (from $s_0$). For comparison, signal intensity data was also analyzed by the Threshold Method.

A comparison of the accuracy and reproducibility of Threshold Method and the P/B Method (from $s_0$) for samples with 50,000 copy numbers/µl is found in Table 7, and a comparison for samples with 500 copy numbers/µl is found in Table 8.

TABLE 7

Quantitation of CMV at 50,000 copies/µl

| n = 6 | Threshold Method | P/B Method (from $s_o$) |
|---|---|---|
| Mean | 60,386 | 51,144 |
| SD | 7,503 | 4,420 |
| CV (%) | 12 | 9 |

TABLE 8

Quantitation of CMV at 500 copies/µl

| n = 6 | Threshold Method | P/B Method (from $s_o$) |
|---|---|---|
| Mean | 467 | 395 |
| SD | 67 | 65 |
| CV (%) | 14 | 17 |

The linearities of amount of initial target NA estimated by the Threshold Method and the P/B Method (from $s_0$) for CMV were very comparable to that demonstrated in Example 2.

Example 4

Quantitation for Polyomavirus BK (BKV) DNA

Quantified BKV genomic DNA (Advanced Biotechnologies, Inc.) was diluted in TE buffer to 1, 10, 100, 1,000, 10,000, and 100,000 copy numbers/per reaction. The diluted DNA samples were amplified by Simplexa BKV real-time PCR assay on an ABI7500 system (Applied Biosystems, Inc.).

The Simplexa BKV real-time PCR assay used a primer mix containing BKV and IC primer pairs. The concentration is 3000 nM for BKV primer pair and 1500 nM for IC primer pair in the primer mix. The sequences of the primer were listed in the Table 9.

TABLE 9

| BKV and IC sequences | |
|---|---|
| BK4T Scorpion™ | Quencher-AGCTGCTATAGGCCTAACTCCTCAAACAT-ATAGCAGCT (SEQ ID NO: 10) -FAM-AATAGCCCCAGGAGCACCA (SEQ ID NO: 11) |
| BK4-3P Reverse | CTGTAGAGGGCATAACAAGTACCTCA (SEQ ID NO: 12) |
| IC Dx2 Scorpion™ | Quencher-TGCGAACTGGCAAGCT (SEQ ID NO: 4) -Q670-ATTCGCCCTTTGTTTCGACCTA (SEQ ID NO: 5) |
| IC Reverse | CCGACGACTGACGAGCAA (SEQ ID NO: 6) |

PCR reactions consisted of the same as described in Example 2.

Amplification was carried out by the same method and instrument as described in Example 2. BKV signal (FAM) was collected from channel A, and IC signal (Q670) was collected from channel E on the ABI7500 real-time PCR instrument. Signal intensity data was collected for eight replicates of each diluted DNA sample.

The dilution series was used to demonstrate the linearity of amounts of initial target NA estimated by the P/B Method (from $s_0$). For comparison, signal intensity data was also analyzed by the Threshold Method.

A comparison of the accuracy and reproducibility of Threshold Method and the P/B Method (from $s_0$) for samples with 10,000 copy numbers/µl is found in Table 10.

TABLE 10

Quantitation of BKV at 10,000 copies/µl

| n = 8 | Threshold Method | P/B Method (from $s_o$) |
|---|---|---|
| Mean | 8,458 | 9,035 |
| SD | 1937 | 1303 |
| CV (%) | 22.9 | 14.4 |

The linearities of amount of initial target NA estimated by the Threshold Method and the P/B Method (from $s_0$) for BKV were very comparable to that demonstrated in Example 2.

Example 5

Quantitation for RNAse P DNA and Quantitation Reproducibility

A RNAse P DNA test plate (an instrument calibration plate provided by ABI, P/N 4350583) was used for this study. The test plate includes 20 pre-diluted RNAse P target DNA standards and 36 replicates each of 5,000 and 10,000 copies/per reaction. The DNA was amplified by ABI's TaqMan chemistry included in the test plate, by using default thermal program (50° C. for 2 min for one cycle, 95° C. for 10 min for one cycle, 95° C. for 30 sec for one cycle and 60° C. for 60 sec for 45 cycles) in the ABI7500 real-time PCR instrument. Signal intensity data were analyzed by the Threshold Method and the P/B Method (from $s_0$).

A comparison of the accuracy and reproducibility of the Threshold Method and the P/B Method (from $s_0$) for samples with 5,000 copy numbers/µl is found in Table 11, and a comparison for samples with 10,000 copy numbers/µl is found in Table 12.

TABLE 11

Quantitation of RNAse at 5,000 copies/µl

| n = 36 | Threshold Method | P/B Method (from $s_o$) |
|---|---|---|
| Mean | 4,912 | 5,082 |
| SD | 255 | 228 |
| CV (%) | 5.19 | 4.50 |

TABLE 12

Quantitation of RNAse at 10,000 copies/µl

| n = 8 | Threshold Method | P/B Method (from $s_o$) |
|---|---|---|
| Mean | 10,216 | 10,182 |
| SD | 364 | 336 |
| CV (%) | 3.56 | 3.30 |

The linearities of amount of initial target NA estimated by the Threshold Method and the P/B Method (from $s_0$) for RNAse P DNA were very comparable to that demonstrated in Example 2.

Example 6

Quantitation for Herpes Simplex Virus Types 1 and 2 (HSV-1 and -2) in Clinical Samples A panel of clinical samples (n=57) submitted for HSV1 and 2 testing at Focus Reference Laboratory was tested by Simplexa HSV1 &2 assay on an ABI7500 system (Applied Biosystems, Inc.). Genomic DNA was isolated from the samples using an automated extraction instrument, MagNA Pure LC system (Roche) and MagNA Pure LC Total Nucleic Acid Isolation kit (Roche).

The Simplexa HSV1&2 assay used a primer mix containing HSV-1, HSV-2 and IC primer pairs. The concentration is 3000 nM for HSV-1 primer pair, 4000 nM for HSV-2 primer pair, and 1000 nM for IC primer pair in the primer mix. The sequences of the primer were listed in the Table 13.

TABLE 13

HSV-1, HSV-2 and IC sequences

| | |
|---|---|
| HSV-1 Scorpion™ | Quencher-AGCGGC CTC CGG GTG CCC GGC CA GCCGCT (SEQ ID NO: 13) -JOE-GAG GAC GAG CTG GCC TTT C (SEQ ID NO: 14) |
| HSV-2-FP-D2 Scorpion™ | Quencher-ACGCGCGTC TTC CGG GCG TTC CGC GACC GCGCGT (SEQ ID NO: 15) -FAM-GAG GAC GAG CTG GCC TTT C (SEQ ID NO: 16) |
| HSV-1/2 RP1 reverse | GGT GGT GGA CAG GTC GTA GAG (SEQ ID NO: 17) |
| IC Dx2 Scorpion™ | Quencher-TGCGAACTGGCAAGCT (SEQ ID NO: 4) -CFR610-ATTCGCCCTTTGTTTCGACCTA (SEQ ID NO: 5) |
| IC Reverse | CCGACGACTGACGAGCAA (SEQ ID NO: 6) |

PCR reactions consisted of the same as described in Example 2.

Amplification was carried out by the same method and instrument as described in Example 2. HSV-1 signal (JOE) was collected from channel B, HSV-2 signal (FAM) was collected from channel A and IC signal (CFR610) was collected from channel D of the ABI7500 real-time PCR instrument. Signal intensity data was collected for each sample and used to estimate the amounts of initial target NA by the Threshold Method, the P/B Method (from $s_0$), and the P/C Method.

Before quantitative analysis, qualitative results were analyzed by the Threshold Method and the P/B Method (from $s_0$). The positive and negative agreement of the two methods was compared (see Table 14). Each method, when used for qualitative determination, demonstrated 100% concordance for all HSV samples.

TABLE 14

Qualitative HSV-1 and -2 Result Comparison

| P/B Method (from $s_o$) | Threshold Method positive | Negative | sum |
|---|---|---|---|
| HSV-1 (n = 57) | | | |
| positive | 24 | 0 | 24 |
| negative | 0 | 33 | 33 |
| sum | 24 | 33 | 57 |
| HSV-2 (n = 57) | | | |
| positive | 25 | 0 | 25 |
| negative | 0 | 32 | 32 |
| sum | 25 | 32 | 57 |

Figure 7:
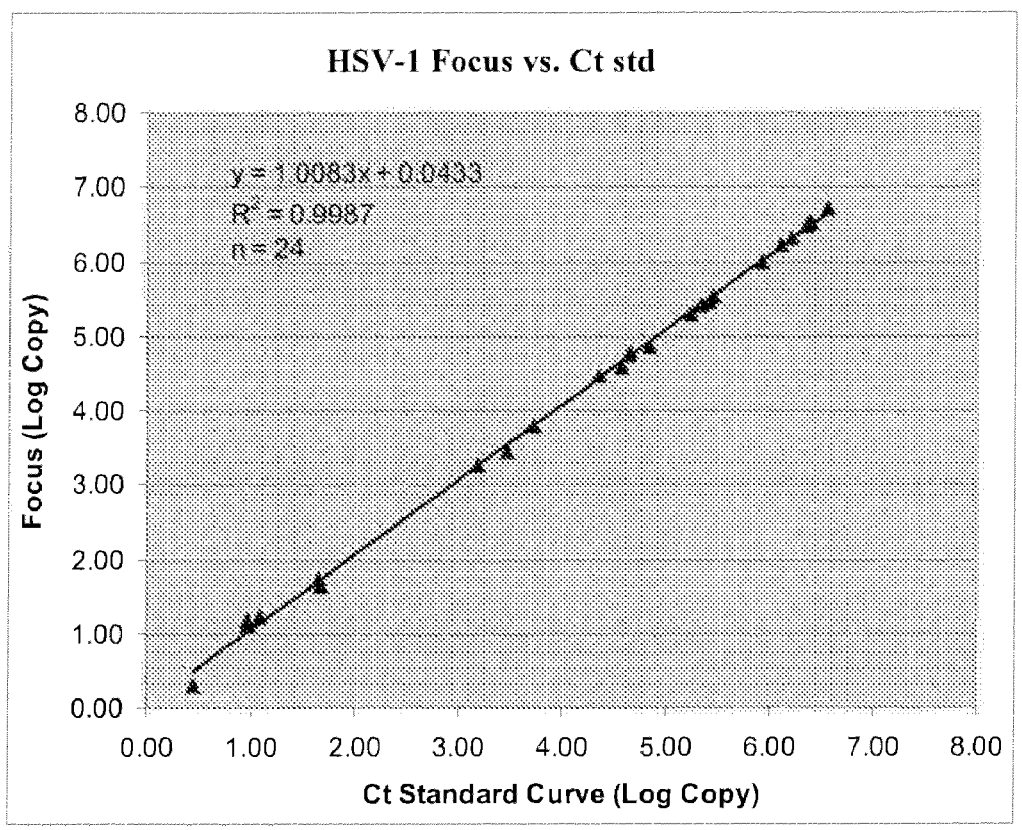
FIG. 7 shows the correlation of HSV-1 quantitation by the threshold standard curve method (x-axis), and an embodiment of the present invention utilizing the two parameter chemical model ($s_0$) (y-axis). Details are discussed in Example 6.
Figure 8:
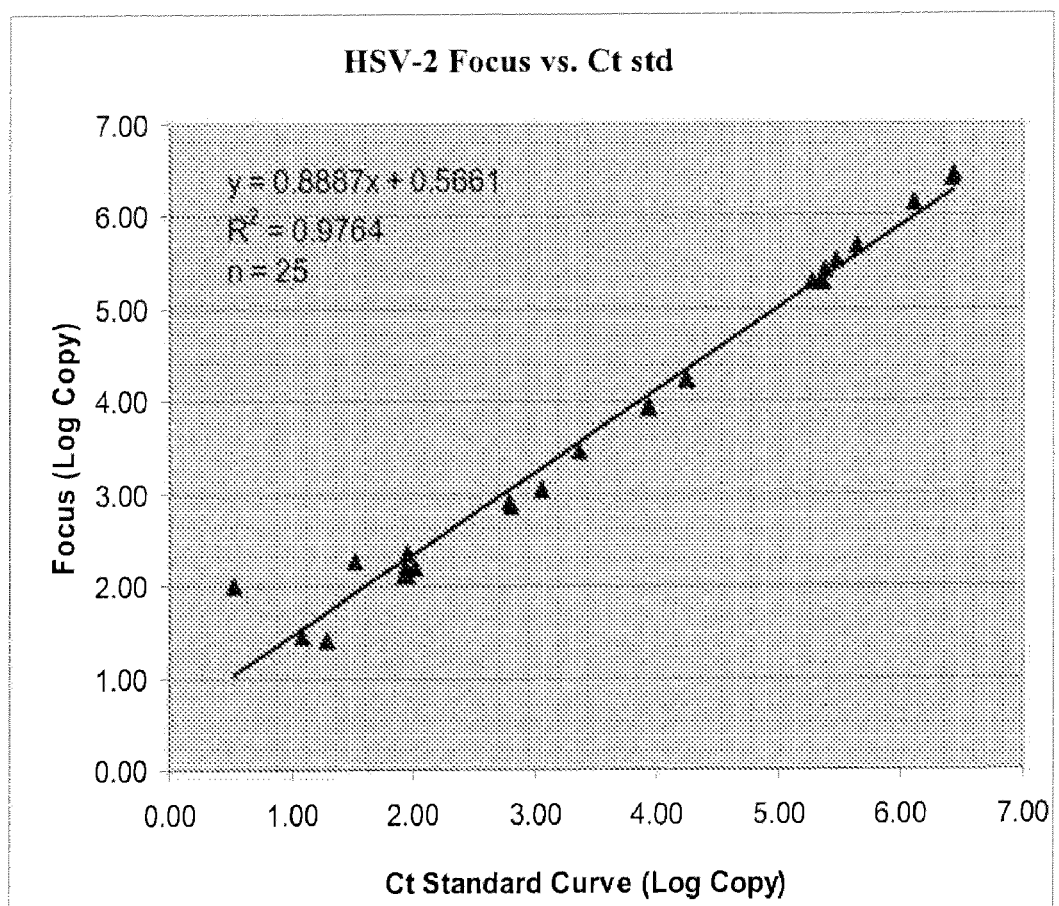
FIG. 8 shows the correlation of HSV-2 quantitation the threshold standard curve method (x-axis), and an embodiment of the present invention utilizing the two parameter chemical model ($s_0$) (y-axis). Details are discussed in Example 6.

Samples that qualitatively tested positive for HSV-1 (n=24) and HSV-2 (n=25) were further analyzed quantitatively by the Threshold Method, the P/B Method (from $s_0$), and the P/C Method, Comparative data for the three estimation methods are shown in Tables 15 and 16 for HSV1 and HSV2, respectively. FIGS. 7 and 8 illustrate the correlation of quantitation by the Threshold Method, and the P/B Method (from $s_0$), respectively,

TABLE 15

Estimated amount of initial target NA in HSV1 Samples

| Sample | Threshold Method | P/B Method (from $s_o$) | P/C Method |
|---|---|---|---|
| H1-1 | 9 | 13 | 11 |
| H1-2 | 21,985 | 28293 | 23140 |
| H1-3 | 45 | 53 | 56 |
| H1-4 | 2,207,380 | 2977287 | 2259892 |
| H1-5 | 12 | 17 | 13 |
| H1-6 | 9 | 15 | 10 |
| H1-7 | 2,897 | 2765 | 3056 |
| H1-8 | 257,466 | 282202 | 270287 |
| H1-9 | 284,656 | 327870 | 276714 |
| H1-10 | 44,800 | 56423 | 46445 |
| H1-11 | 1,589,580 | 2065654 | 1734360 |
| H1-12 | 2,421,110 | 3245448 | 2598436 |
| H1-13 | 1,501 | 1850 | 1502 |
| H1-14 | 47 | 44 | 50 |
| H1-15 | 1,265,970 | 1697347 | 1332712 |
| H1-16 | 67,998 | 72651 | 70177 |
| H1-17 | 823,979 | 970924 | 843479 |
| H1-18 | 212,986 | 255704 | 229857 |
| H1-19 | 36,790 | 37385 | 36578 |
| H1-20 | 3 | 2 | 3 |
| H1-21 | 3,529,360 | 4995628 | 3926455 |
| H1-22 | 42,628 | 55975 | 49484 |
| H1-23 | 174,049 | 195894 | 173026 |
| H1-24 | 5,201 | 6154 | 5878 |

TABLE 10

Estimated amount of initial target NA in HSV1 Samples

| Sample | Threshold Method | P/B Method (from $s_o$) | P/C Method |
|---|---|---|---|
| H1-1 | 3 | 100 | 159 |
| H2-1 | 85 | 157 | 122 |
| H2-2 | 90 | 222 | 107 |
| H2-3 | 12 | 29 | 15 |
| H2-4 | 618 | 811 | 699 |
| H2-5 | 33 | 189 | 53 |
| H2-6 | 19 | 26 | 20 |
| H2-7 | 8,532 | 8342 | 8631 |
| H2-8 | 293,510 | 327443 | 327574 |

TABLE 10-continued

Estimated amount of initial target NA in HSV1 Samples

| Sample | Threshold Method | P/B Method (from $s_o$) | P/C Method |
|---|---|---|---|
| H2-9 | 2,332 | 2814 | 2578 |
| H2-10 | 17,420 | 17105 | 17171 |
| H2-11 | 2,664,040 | 2762575 | 2913078 |
| H2-12 | 8,201 | 8321 | 8605 |
| H2-13 | 181,092 | 192221 | 195365 |
| H2-14 | 238,659 | 264466 | 256857 |
| H2-15 | 17,142 | 16888 | 18053 |
| H2-16 | 641 | 733 | 691 |
| H2-17 | 1,277,940 | 1405902 | 1442496 |
| H2-18 | 439,061 | 467888 | 485901 |
| H2-19 | 2,544,640 | 2594372 | 2768014 |
| H2-20 | 231,880 | 195453 | 224689 |
| H2-21 | 83 | 127 | 92 |
| H2-22 | 89 | 132 | 119 |
| H2-23 | 1,135 | 1083 | 1226 |
| H2-24 | 104 | 157 | 128 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

That which is claimed is:

1. A method of estimating the initial amount of a target nucleic acid in a sample prior to nucleic acid amplification by polymerase chain reaction (PCR), said method comprising:
   i) performing PCR on said sample;
   ii) obtaining signal intensity data from the performed PCR across a range of PCR cycles;
   iii) modeling the signal intensity data with a phenomenological model and a chemical model, thereby estimating the initial amount of target nucleic acid in the sample; and
   iv) outputting the estimate of the initial amount of target nucleic acid in the sample to a user or computer readable format;

wherein said chemical model is selected from the group consisting of:
   a)  $P_3 := s^2 E^3 - (s^2 + (1-D+2q)s)E^2 + q(2s+q+1)E - q^2 = 0$, wherein:
   $S = K_2 [S]_T$, $$D = \frac{K_4}{K_2 (K_1 [p]_T)^2},$$

and
   $[S]_T = [s] + [h] + [r] + [d]$;
   $P_4 := S^3 E^4 -$
   $(S^3 + (p + 2\kappa q + 2\kappa)s^2)E^3 +$
   $((p + 2\kappa q + \kappa) + ((2\kappa q + \kappa)p + \kappa + (-\kappa q - \kappa)^2)s)E^2 -$
   $((2\kappa q p + (\kappa q + \kappa)\kappa q)s + (\kappa q + \kappa)\kappa q p + \kappa^2 q^2)E +$
   $\kappa^2 q^2 p = 0$, wherein:
   $s = K_1 [s]_T$,
   $\kappa = K_1 / K_2$, and
   $[S]_T = [s] + [h] + [r]$;
and
   C) $P_2 := sE^2 - (s+q+1)E + q = 0$, wherein:
   $s = K_2 [s]_T$, and
   $[s]_T = [s] + [h] + [r]$;
wherein in all of the above formulae:
E is the amplification efficiency,
$p = K_1 [p]_T$,
$q = K_2 [q]_T$,
$[p]_T = [p] + [h] + [r]$,
$[q]_T = [q] + [r]$, $$K_1 = \frac{[h_0]}{[s][p]},$$

$$K_2 = \frac{[r_0]}{[q][h_0]},$$

$$K_4 = \frac{[d]}{[s][s^*]} = \frac{[d]}{[s]^2},$$

[s] denotes the equilibrium concentration of single stranded nucleic acid,
[p] denotes the equilibrium concentration of primer,
[q] denotes the equilibrium concentration of polymerase,
[h] denotes the equilibrium concentration of primer-template duplex, with subscripts on h indicating the number of nucleotides extending the primer and no subscripts indicating a fully extended primer,
[r] denotes the equilibrium concentration of reaction complex, with subscripts on r indicating the number of nucleotides extending the primer and no subscripts indicating a fully extended primer,
[s*] denotes the equilibrium concentration of single stranded nucleic acid complementary to s, and
[d] denotes the equilibrium concentration of double-stranded nucleic acid.

2. The method of claim 1, wherein said modeling further comprises estimating the amount of target nucleic acid generated in a reaction mixture in at least two PCR cycles.

3. The method of claim 1, wherein said chemical model is the formula recited in part (a) of claim 1.

4. The method of claim 3, further comprising estimating the initial amount of target nucleic acid from the initial reduced single stranded nucleic acid concentration, $s_0$, by the formula $$s_0 = x_0 \frac{K_2}{NV},$$

wherein $x_0$ is the initial amount of target nucleic acid in the sample, N is Avogadro's number, and V is the sample volume.

5. The method of claim 1, wherein said chemical model is the formula recited in part (b) of claim 1.

6. The method of claim 5, further comprising estimating the initial amount of target nucleic acid from the initial reduced single stranded nucleic acid concentration, $s_0$, by the formula $$s_0 = x_0 \frac{K_1}{NV},$$

wherein $x_0$ is the initial amount of target nucleic acid in the sample, N is Avogadro's number, and V is the sample volume.

7. The method of claim 1, wherein said chemical model is the formula recited in part (c) of claim 1.

8. The method of claim 7, further comprising estimating the initial amount of target nucleic acid from the initial reduced single stranded nucleic acid concentration, $s_0$, by the formula $$s_0 = x_0 \frac{K_2}{NV},$$

wherein $x_0$ is the initial amount of target nucleic acid in the sample, N is Avogadro's number, and V is the sample volume.

9. The method of claim 1, wherein modeling the signal intensity with a phenomenological model comprises:
   v) estimating an efficiency $E_0$ using the formula $$E_0 = \max\left[\frac{y_{k-1} + y_k + y_{k+1}}{y_{k-2} + y_{k-1} + y_k} - 1\right],$$

wherein $y_k$ is signal intensity in cycle number k,
   vi) estimating a quantity $Gx_0$ using the formula $Gx_0 = y_{k_{max}}(1+E_0)^{-k_{max}}$, wherein $E_0$ is the efficiency estimated in step (v) and $k_{max}$ is the cycle number k in which $E_0$ is maximized in step (v),
   vii) estimating a cycle-dependent efficiency $E_i$, a background offset a, and a drift constant b using the phenomenological model $$z_k = a + bk + Gx_0 \prod_{i=1}^{k} (1 + E_i),$$

wherein k is the cycle number, $z_k$ is the signal intensity at cycle k, and $Gx_0$ has the value as estimated in step (vi).

10. The method of claim 1, wherein said modeling comprises using a nonlinear least squares curve fitting approximation method for estimating the parameters of the models.

11. The method of claim 10, wherein the nonlinear least squares curve fitting approximation method is a Levenberg-Marquardt approximation method.

12. The method of claim 1, further comprising identifying a subset of signal intensity data generated across a range of PCR cycles for modeling.

13. The method of claim 12, wherein identifying said subset comprises identifying a range of PCR cycles beginning before replication is apparent and ending at a cycle where the amplification efficiency, $E_k$, has decreased to a predetermined absolute lower limit or a relative amount from the initial amplification efficiency, $E_1$.

14. The method of claim 13, wherein the ending cycle is a cycle having an absolute amplification efficiency between 10% and 50%.

15. The method of claim 14, wherein the subset comprises the ending cycle and the preceding five to fifteen cycles.

16. A method of estimating the initial amount of a target nucleic acid in a sample prior to nucleic acid amplification by polymerase chain reaction, said method comprising:
   i) performing PCR on said sample;
   ii) obtaining signal intensity data from the performed PCR across a range of PCR cycles;
   iii) modeling the signal intensity data with a phenomenological model and a chemical model, thereby estimating the initial amount of target nucleic acid in the sample; and
   iv) outputting the estimate of the initial amount of target nucleic acid in the sample to a user or computer readable format;
wherein modeling the signal intensity with a phenomenological model comprises:
   v) estimating an efficiency $E_0$ using the formula $$E_0 = \max\left[\frac{y_{k-1} + y_k + y_{k+1}}{y_{k-2} + y_{k-1} + y_k} - 1\right],$$

wherein $y_k$ is signal intensity in cycle number k,
   vi) estimating a quantity $Gx_0$ using the formula $Gx_0 = y_{k_{max}}(1+E_0)^{-k_{max}}$, wherein $E_0$ is the efficiency estimated in step (v) and $k_{max}$ is the cycle number k in which $E_0$ is maximized in step (v),
   vii) estimating a cycle-dependent efficiency $E_i$, a background offset a, and a drift constant b using the phenomenological model $$z_k = a + bk + Gx_0 \prod_{i=1}^{k} (1 + E_i),$$

wherein k is the cycle number, $z_k$ is the signal intensity at cycle k, and $Gx_0$ has the value as estimated in step (vi).

17. The method of claim 16, wherein said chemical model is selected from the group consisting of:
   a) $P_3 := s^2E^3 - (s^2+(1-D+2q)s)E^2 + q(2s+q+1)E - q^2 = 0$, wherein:
      $S = K_2[S]_T$, $$D = \frac{K_4}{K_2(K_1[p]_T)^2},$$

and
      $[S]_T = [s]+[h]+[r]+[d]$;
   $P_4 := S^3E^4 -$
      $(S^3+(p+2\kappa q+2\kappa)s^2)E^3 +$
      $((p+2\kappa q+\kappa)+((2\kappa q+\kappa)p+\kappa+(-\kappa q-\kappa)^2)s)E^2 -$
      $((2\kappa qp+(\kappa q+\kappa)\kappa q)s+(\kappa q+\kappa)\kappa qp+\kappa^2 q)E +$
      $\kappa^2 q^2 p = 0$, wherein:
      $s = K_1[s]_T$,
      $\kappa = K_1/K_2$, and
      $[S]_T = [s]+[h]+[r]$;
   and
   C) $P_2 := sE^2 - (s+q+1)E + q = 0$, wherein:
      $s = K_2[s]_T$, and
      $[s]_T = [s]+[h]+[r]$;
wherein in all of the above formulae:
   E is the amplification efficiency,
   $p = K_1[p]_T$, $q = K_2[q]_T$,
$[p]_T = [p]+[h]+[r]$,
$[q]_T = [q]+[r]$, $$K_1 = \frac{[h_0]}{[s][p]},$$

[s] denotes the equilibrium concentration of single stranded nucleic acid,
[p] denotes the equilibrium concentration of primer,
[q] denotes the equilibrium concentration of polymerase,
[h] denotes the equilibrium concentration of primer-template duplex, with subscripts on h indicating the number of nucleotides extending the primer and no subscripts indicating a fully extended primer,
[r] denotes the equilibrium concentration of reaction complex, with subscripts on r indicating the number of nucleotides extending the primer and no subscripts indicating a fully extended primer,
[s*] denotes the equilibrium concentration of single stranded nucleic acid complementary to s, and
[d] denotes the equilibrium concentration of double-stranded nucleic acid.

18. A computer program product embodied on a non-transitory computer-readable medium, the computer program product comprising:
(i) computer code that causes a processor to receive a signal intensity indicative of an amount of target nucleic acid present in a sample at a multiple times during a PCR amplification;
(ii) computer code that causes a processor to estimate the initial target nucleic acid in the sample using a phenomenological model and a chemical model; and
(iii) computer code that causes a processor to output the estimate of initial target nucleic acid in the sample to a user or computer readable media;
wherein the computer code for estimating the initial target nucleic acid in the sample using a phenomenological model comprises:
iv) computer code that causes a processor to estimate an efficiency $E_0$ using the formula $$E_0 = \max\left[\frac{y_{k-1} + y_k + y_{k+1}}{y_{k-2} + y_{k-1} + y_k} - 1\right],$$

wherein $y_k$ is signal intensity in cycle number k,
v) computer code that causes a processor to estimate a quantity $Gx_0$ using the formula $Gx_0 = y_{k_{max}}(1+E_0)^{-k_{max}}$, wherein $E_0$ is the efficiency estimated by the code of (iv) and $k_{max}$ is the cycle number k in which $E_0$ is maximized by the code of (iv),
vi) computer code that causes a processor to estimate a cycle-dependent efficiency $E_i$, a background offset a, and a drift constant b using the phenomenological model $$z_k = a + bk + Gx_0 \prod_{i=1}^{k}(1+E_i),$$

wherein k is the cycle number, $z_k$ is the signal intensity at cycle k, and $Gx_0$ has the value as estimated in step (v); and wherein said chemical model is selected from the group consisting of:

a) $P_3 := s^2E^3 - (s^2+(1-D+2q)s)E^2 + q(2s+q+1)E - q^2 = 0$, wherein:
$S = K_2[S]_T$, $$D = \frac{K_4}{K_2(K_1[p]_T)^2},$$

and
$[S]_T = [s]+[h]+[r]+[d]$;
$P_4 := S^3E^4 -$
$(S^3+(p+2\kappa q+2\kappa)s^2)E^3 +$
$((p+2\kappa q+\kappa)+((2\kappa q+\kappa)p+\kappa+(-\kappa q-\kappa)^2)s)E^2 -$
$((2\kappa qp+(\kappa q+\kappa)\kappa q)s+(\kappa q+\kappa)\kappa qp+\kappa^2 q)E +$
$\kappa^2 q^2 p = 0$, wherein:
$s = K_1[s]_T$,
$\kappa = K_1/K_2$, and
$[S]_T = [s]+[h]+[r]$;
and
C) $P_2 := sE^2 - (s+q+1)E + q = 0$, wherein:
$s = K_2[s]_T$, and
$[s]_T = [s]+[h]+[r]$;
wherein in all of the above formulae:
E is the amplification efficiency,
$p = K_1[p]_T$,
$q = K_2[q]_T$,
$[p]_T = [p]+[h]+[r]$,
$[q]_T = [q]+[r]$, $$K_1 = \frac{[h_0]}{[s][p]},$$

$$K_2 = \frac{[r_0]}{[q][h_0]},$$

$$K_4 = \frac{[d]}{[s][s^*]} = \frac{[d]}{[s]^2},$$

[s] denotes the equilibrium concentration of single stranded nucleic acid,
[p] denotes the equilibrium concentration of primer,
[q] denotes the equilibrium concentration of polymerase,
[h] denotes the equilibrium concentration of primer-template duplex, with subscripts on h indicating the number of nucleotides extending the primer and no subscripts indicating a fully extended primer,
[r] denotes the equilibrium concentration of reaction complex, with subscripts on r indicating the number of nucleotides extending the primer and no subscripts indicating a fully extended primer,
[s*] denotes the equilibrium concentration of single stranded nucleic acid complementary to s, and
[d] denotes the equilibrium concentration of double-stranded nucleic acid.

19. The computer program product of claim 18, wherein said input is received from a user.

20. The computer program product of claim 18, wherein said input is received from a device.

21. An apparatus comprising a processor, and a memory unit coupled to the processor that comprises:
(i) computer code that causes the processor to receive a signal intensity indicative of an amount of target nucleic acid present in a sample at a multiple times during a PCR amplification;
(ii) computer code that causes the processor to estimate the initial target nucleic acid in the sample using a phenomenological model and a chemical model; and (iii) computer code that causes the processor to output the estimate of initial target nucleic acid in the sample to a user or computer readable media;

wherein the computer code for estimating the initial target nucleic acid in the sample using a phenomenological model comprises:

iv) computer code that causes the processor to estimate an efficiency $E_0$ using the formula $$E_0 = \max\left[\frac{y_{k-1} + y_k + y_{k+1}}{y_{k-2} + y_{k-1} + y_k} - 1\right],$$

wherein $y_k$ is signal intensity in cycle number k, v) computer code that causes the processor to estimate a quantity $Gx_0$ using the formula $Gx_0 = y_{k_{max}}(1+E_0)^{-k_{max}}$, wherein $E_0$ is the efficiency estimated by the code of (iv) and $k_{max}$ is the cycle number k in which $E_0$ is maximized by the code of (iv), vi) computer code that causes the processor to estimate a cycle-dependent efficiency $E_i$, a background offset a, and a drift constant b using the phenomenological model $$z_k = a + bk + Gx_0 \prod_{i=1}^{k}(1+E_i),$$

wherein k is the cycle number, $z_k$ is the signal intensity at cycle k, and $Gx_0$ has the value as estimated by the code of (v); and wherein said chemical model is selected from the group consisting of:

a) $P_3 := s^2E^3 - (s^2+(1-D+2q)s)E^2 + q(2s+q+1)E - q^2 = 0$, wherein:
$S = K_2[S]_T$, $$D = \frac{K_4}{K_2(K_1[p]_T)^2},$$

and
$[S]_T = [s]+[h]+[r]+[d]$;
$P_4 := S^3E^4 -$
$(S^3+(p+2\kappa q+2\kappa)s^2)E^3 +$
$((p+2\kappa q+\kappa)+((2\kappa q+\kappa)p+\kappa+(-\kappa q-\kappa)^2)s)E^2 -$
$((2\kappa qp+(\kappa q+\kappa)\kappa q)s+(\kappa q+\kappa)\kappa qp+\kappa^2 q)E +$
$\kappa^2 q^2 p = 0$, wherein:
$s = K_1[s]_T$,
$\kappa = K_1/K_2$, and
$[S]_T = [s]+[h]+[r]$;
and
C) $P_2 := sE^2 - (s+q+1)E + q = 0$, wherein:
$s = K_2[s]_T$, and
$[s]_T = [s]+[h]+[r]$;

wherein in all of the above formulae:
E is the amplification efficiency,
$p = K_1[p]_T$,
$q = K_2[q]_T$,
$[p]_T = [p]+[h]+[r]$,
$[q]_T = [q]+[r]$, $$K_1 = \frac{[h_0]}{[s][p]},$$

$$K_2 = \frac{[r_0]}{[q][h_0]},$$

$$K_4 = \frac{[d]}{[s][s^*]} = \frac{[d]}{[s]^2},$$

[s] denotes the equilibrium concentration of single stranded nucleic acid,

[p] denotes the equilibrium concentration of primer,

[q] denotes the equilibrium concentration of polymerase,

[h] denotes the equilibrium concentration of primer-template duplex, with subscripts on h indicating the number of nucleotides extending the primer and no subscripts indicating a fully extended primer,

[r] denotes the equilibrium concentration of reaction complex, with subscripts on r indicating the number of nucleotides extending the primer and no subscripts indicating a fully extended primer,

[s*] denotes the equilibrium concentration of single stranded nucleic acid complementary to s, and

[d] denotes the equilibrium concentration of double-stranded nucleic acid.

22. The apparatus of claim 21, wherein said input is received from a user.

23. The apparatus of claim 21, wherein said input is received from a device.

\* \* \* \* \*

UNITED STATES PATENT AND TRADEMARK OFFICE
CERTIFICATE OF CORRECTION

PATENT NO.       : 8,346,485 B2
APPLICATION NO.  : 12/330442
DATED            : January 1, 2013
INVENTOR(S)      : Benedict G. Archer It is certified that error appears in the above-identified patent and that said Letters Patent is hereby corrected as shown below:

IN THE CLAIMS

The exact claim and line number where the errors in the issued patent are:

Claim 1, Column 39, line 40

Change "$S=K_2[S]_T$" to --$s=K_2[s]_T$--

Claim 1, Column 39, line 47

Change "$[S]_T$" to --$[s]_T$--

Claim 1, Column 39, line 48

Change "$P_4:=S^3E^4$-" to --b) $P_4:=s^3E^4$--

Claim 1, Column 39, line 49

Change "$S^3$" to --$s^3$--

Claim 1, Column 39, line 50

Change "$((p+2\kappa q+\kappa)+((2\ \kappa q+\kappa)p+\kappa+(-\kappa q-\kappa)^2)s)E^2$-" to --$((p+2\kappa q+\kappa)s^2+((2\kappa q+\kappa)p+\kappa+(-\kappa q-\kappa)^2)s)E^2$--

Signed and Sealed this
Nineteenth Day of March, 2013

Teresa Stanek Rea
*Acting Director of the United States Patent and Trademark Office*

CERTIFICATE OF CORRECTION (continued)

Claim 1, Column 39, line 53

Change "s=K$_1$[s]$_T$" to --s=$K_1$[s]$_T$--

Claim 1, Column 39, line 54

Change "κ=K$_1$/K$_2$" to --$\kappa=K_1/K_2$--

Claim 1, Column 39, line 55

Change "[S]$_T$" to --[s]$_T$--

Claim 1, Column 39, line 58

Change "C)  P$_2$:=sE$^2$" to --c) P$_2$:= sE$^2$--

Claim 1, Column 39, line 59

Change "S = K$_2$[S]$_T$" to --s=$K_2$[s]$_T$--

Claim 1, Column 39, line 64

Change "p=K$_1$[p]$_T$" to --p=$K_1$[p]$_T$--

Claim 1, Column 39, line 65

Change "q=K$_2$[q]$_T$" to --q=$K_2$[q]$_T$--

Claim 17, Column 42, line 44

Change "S=K$_2$[S]$_T$" to --s=$K_2$[s]$_T$--

Claim 17, Column 42, line 52

Change "[S]$_T$" to --[s]$_T$--

Claim 17, Column 42, line 53

Change "P$_4$:=S$^3$E$^4$-" to --b) P$_4$:=s$^3$E$^4$--

Claim 17, Column 42, line 54

Change "$S^3$" to --$s^3$--

Claim 17, Column 42, line 55

Change "$((p+2\kappa q+\kappa)+((2\kappa q+\kappa)p+\kappa+(-\kappa q-\kappa)^2)s)E^2$-" to --$((p+2\kappa q+\kappa)s^2+((2\kappa q+\kappa)p+\kappa+(-\kappa q-\kappa)^2)s)E^2$--

Claim 17, Column 42, line 58

Change "$s=K_1[s]_T$" to --$s=K_1[s]_T$--

Claim 17, Column 42, line 59

Change "$\kappa=K_1/K_2$" to --$\kappa=K_1/K_2$--

Claim 17, Column 42, line 60

Change "$[S]_T$" to --$[s]_T$--

Claim 17, Column 42, line 62

Change "C) $P_2:=sE^2$" to --c) $P_2:=sE^2$--

Claim 17, Column 42, line 63

Change "$S = K_2[S]_T$" to --$s=K_2[s]_T$--

Claim 17, Column 42, line 67

Change "$p=K_1[p]_T$" to --$p=K_1[p]_T$--

Claim 17, Column 43, line 1

Change "$q=K_2[q]_T$" to --$q=K_2[q]_T$--

Claim 17, Column 43, line 6

Part of the equation is missing. After the equation for $K_1$, insert the equations for $K_2$ and $K_4$ $$K_2 = \frac{[r_0]}{[q][h_0]},$$

$$K_4 = \frac{[d]}{[s][s^*]} = \frac{[d]}{[s]^2},$$

Claim 18, Column 44, line 3

Change "S=K$_2$[S]$_T$" to --s=$K_2$[s]$_T$--

Claim 18, Column 44, line 10

Change "[S]$_T$" to --[s]$_T$--

Claim 18, Column 44, line 11

Change "P$_4$:=S$^3$E$^4$-" to --b) P$_4$:=s$^3$E$^4$--

Claim 18, Column 44, line 12

Change "S$^3$" to --s$^3$--

Claim 18, Column 44, line 13

Change "((p+2$\kappa q$+$\kappa$)+((2 $\kappa q$+$\kappa$)p+$\kappa$+(-$\kappa q$-$\kappa$)$^2$)s)E$^2$-" to --((p+2$\kappa q$+$\kappa$)s$^2$+((2$\kappa q$+$\kappa$)p+$\kappa$+(-$\kappa q$-$\kappa$)$^2$)s)E$^2$--

Claim 18, Column 44, line 16

Change "s=K$_1$[s]$_T$" to --s=$K_1$[s]$_T$--

Claim 18, Column 44, line 17

Change "$\kappa=K_1/K_2$" to $-\kappa=K_1/K_2-$

Claim 18, Column 44, line 18

Change "$[S]_T$" to $-[s]_T-$

Claim 18, Column 44, line 20

Change "C)  $P_2:=sE^2$" to $-c)\ P_2:=sE^2-$

Claim 18, Column 44, line 21

Change "$S = K_2[S]_T$" to $-s=K_2[s]_T-$

Claim 18, Column 44, line 25

Change "$p=K_1[p]_T$" to $-p=K_1[p]_T-$

Claim 18, Column 44, line 26

Change "$q=K_2[q]_T$" to $-q=K_2[q]_T-$

Claim 21, Column 45, line 43

Change "$S=K_2[S]_T$" to $-s=K_2[s]_T-$

Claim 21, Column 46, line 2

Change "$[S]_T$" to $-[s]_T-$

Claim 21, Column 46, Line 3

Change "$P_4:=S^3E^4-$" to $-b)\ P_4:=s^3E^4-$

Claim 21, Column 46, line 4

Change "$S^3$" to $-s^3-$

Claim 21, Column 46, Line 5

Change "((p+2κq+κ)+((2 κq+κ)p+κ+(-κq-κ)²)s)E²-" to --((p+2κq+κ)s²+((2κq+κ)p+κ+(-κq-κ)²)s)E²--

Claim 21, Column 46, line 8

Change "s=K$_1$[s]$_T$" to --s=$K_1$[s]$_T$--

Claim 21, Column 46, line 9

Change "κ=K$_1$/K$_2$" to --κ=$K_1$/$K_2$--

Claim 21, Column 46, line 10

Change "[S]$_T$" to --[s]$_T$--

Claim 21, Column 46, line 12

Change "C) P$_2$:=sE²" to --c) P$_2$:= sE²--

Claim 21, Column 46, line 13

Change "S = K$_2$[S]$_T$" to --s=$K_2$[s]$_T$--

Claim 21, Column 46, line 16

Change "p=K$_1$[p]$_T$" to --p=$K_1$[p]$_T$--

Claim 21, Column 46, line 17

Change "q=K$_2$[q]$_T$" to --q=$K_2$[q]$_T$--

SEQUENCE LISTING

<160> NUMBER OF SEQ ID NOS: 17

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agcggagtga aacggtacaa actccgct                                          28

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttattgttt acgcttcccg ctgaa                                             25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcccgtttgc ttactctgga taa                                               23

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgcgaactgg caagct                                                     16

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
attcgccctt tgtttcgacc ta                                              22

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ccgacgactg acgagcaa                                                   18

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
aggcgtgcag caccaacacg tggctacaca cgcct                                35

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
taacgattac gaccgctaaa acc                                             23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cagcggaaac accgttacaa                                                 20

<210> SEQ ID NO 10
<211> LENGTH: 38

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agctgctata ggcctaactc ctcaaacata tagcagct                          38

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatagcccca ggagcacca                                               19

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgtagaggg cataacaagt acctca                                       26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcggcctcc gggtgcccgg ccagccgct                                    29

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaggacgagc tggcctttc                                               19

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgcgcgtct tccgggcgtt ccgcgaccgc gcgt                              34

<210> SEQ ID NO 16
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 16
gaggacgagc tggcctttc                                                 19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtggtggac aggtcgtaga g                                              21
```